(12) United States Patent
Hession et al.

(10) Patent No.: US 6,252,043 B1
(45) Date of Patent: *Jun. 26, 2001

(54) VASCULAR CELL ADHESION MOLECULE (VCAM) POLYPEPTIDES

(75) Inventors: Catherine A. Hession, South Weymouth; Roy R. Lobb, Westwood; Susan E. Goelz, Winchester; Laurelee Osborn, Brighton; Christopher D. Benjamin, Beverly; Margaret D. Rosa, Winchester, all of MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/310,890

(22) Filed: Sep. 22, 1994

Related U.S. Application Data

(62) Division of application No. 08/035,674, filed on Mar. 23, 1993, now Pat. No. 5,367,056, which is a division of application No. 07/452,675, filed on Dec. 18, 1989, now Pat. No. 5,272,263, which is a continuation-in-part of application No. 07/359,516, filed on Jun. 1, 1989, now abandoned, which is a continuation-in-part of application No. 07/345, 151, filed on Apr. 28, 1989, now Pat. No. 5,217,870.

(51) Int. Cl.[7] .................. C07K 14/705; C07K 14/47; C07K 14/46

(52) U.S. Cl. ........................ 530/350; 530/387.3

(58) Field of Search ................. 530/350, 387.3

(56) References Cited

U.S. PATENT DOCUMENTS

| | | |
|---|---|---|
| 4,752,569 | 6/1988 | Terasaki et al. . |
| 5,011,778 | 4/1991 | Newman et al. . |
| 5,098,833 | * 3/1992 | Lasky . |
| 5,225,538 | * 7/1993 | Capon et al. ............... 530/387.3 |
| 5,284,931 | * 2/1994 | Springer et al. . |

FOREIGN PATENT DOCUMENTS

| | | |
|---|---|---|
| 3 642 096 | 12/1986 | (DK) . |
| 0 330 506 | 8/1989 | (EP) . |
| 0 408 859 | 1/1991 | (EP) . |
| 90/05786 | * 5/1990 | (WO) . |

OTHER PUBLICATIONS

Arfors, K.–E., et al., "A Monoclonal Antibody to the Membrane Glycoprotein Complex CD18 Inhibits Polymorphonuclear Leukocyte Accumulation and Plasma Leakage In Vivo", *Blood*, 69, pp. 338–340 (1987).

Aruffo, A., and B. Seed, "Molecular Cloning of a CD28 cDNA by a High Efficiency COS Cell Expression System", *Proc. Natl. Acad. Sci. USA*, 84, pp. 8573–8577 (1987).

Becker, D., et al., "Proliferation of Human Malignant Melanomas Is Inhibited by Antisense Oligodeoxynucleotides Targeted Against Basic Fibroblast Growth Factor", *EMBO J.*, 8, pp. 3685–3691 (1989).

Benchimol, S., et al., "Carcinoembryonic Antigen, A Human Tumor Marker, Functions as an Intercellular Adhesion Molecule", *Cell*, 57, pp. 327–334 (1989).

Bevilacqua, M.P., et al., "Identification of an Inducible Endothelial–Leukocyte Adhesion Molecule (E–LAM 1) Using Monoclonal Antibodies (Mab)", *Fed. Amer. Soc. Exper. Biol.*, 71st Annual Meeting, Abstr. #514, p. 505 (1987).

Bevilacqua, M.P., et al., "Identification of an Inducible Endothelial–Leukocyte Adhesion Molecule", *Proc. Natl. Acad. Sci. USA*, 84, pp. 9238–9242 (1987b).

Bevilacqua, M.P., et al., "Endothelial Leukocyte Adhesion Molecule 1: An Inducible Receptor for Neutrophils Related to Complement Regulatory Proteins and Lectins", *Science*, 243, pp. 1160–1165 (1989).

Bevilacqua, M.P., et al., "Interleukin 1 Acts on Cultured Human Vascular Endothelium to Increase the Adhesion of Polymorphonuclear Leukocytes, Monocytes, and Related Leukocyte Cell Lines", *J. Clin. Invest.*, 76, pp. 2003–2011 (1985).

Bevilacqua, M.P., et al., "Endothelial–Dependent Mechanisms of Leukocyte Adhesion: Regulation by Interleukin–1 and Tumor Necrosis Factor", *Leukocyte Emigration and Its Sequelae* (S. Karger A.G., Switzerland, 1987a), pp. 79–93.

Bevilacqua, M.P., and M.A. Gimbrone, "Inducible Endothelial Functions in Inflammation and Coagulation", *Seminars in Thrombosis and Hemostasis*, 13, pp. 425–433 (1987).

Breathnach, R. and P. Chambon, "Organization and Expression of Eucaryotic Split Genes Coding for Proteins", *Ann. Rev. Biochem.*, 50, pp. 349–383 (1981).

Brenan, M. and C.R. Parish, "Intracellular Fluorescent Labelling of Cells for Analysis of Lymphocyte Migration", *J. Immun. Meth.*, 74, pp. 31–38 (1984).

Capon, D.J., et al., "Designing CD4 Immunoadhesins for AIDS Therapy", *Nature*, 337, pp. 525–531 (1989).

Carlsson, R., and C. Glad, "Monoclonal Antibodies into the '90s", *Bio/Technology*, 7, pp. 567–573 (Jun. 1989).

Cate, R., et al., "Isolation of the Bovine and Human Genes for Mullerian Inhibiting Substance and Expression of the Human Gene in Animal Cells", *Cell*, 45, pp. 685–698 (1986).

Cech, T.R., "Ribozymes and Their Medical Implications", *J. Amer. Med. Assn.*, 260, pp. 3030–3034 (1988).

Chang et al., "Recombination Following Transformation of *Escherichia coli* by Heteroduplex Plasmid DNA Molecules", *Gene*, 29, pp. 255–261 (1984).

Chen, Y.P., et al., "Molecular Cloning and Characterization of Two Rat Renal Kallikrein Genes", *Biochemistry*, 27, pp. 7189–7196 (1988).

(List continued on next page.)

Primary Examiner—Phillip Gambel
(74) *Attorney, Agent, or Firm*—Timothy P. Linkkila; Biogen, Inc.

(57) ABSTRACT

VCAM1 polypeptides and VCAM11/ICAM fusion proteins are disclosed.

5 Claims, 18 Drawing Sheets

OTHER PUBLICATIONS

Colley, K.J., et al., "Conversion of a Golgi Apparatus Sialyltransferase to a Secretory Protein by Replacement of the NH$_2$–terminal Signal Anchor with a Signal Peptide", *J. Biol. Sci.*, 264, pp. 17619–17622 (1989).

Cotran, R.S., and J.S. Pober, "Endothelial Activation: Its Role in Inflammatory and Immune Reactions", in *Endothelial Cell Biology*, Simionescu and Simionescu, Eds., Plenum Press, New York (1988), pp. 335–347.

Cotran, R.S., et al., "Induction and Detection of a Human Endothelial Activation Antigen In Vivo", *J. Exp. Med.*, 164, pp. 661–666 (1986).

Dana, N., et al., "Mol Surface Glycoprotein: Structure, Function and Clinical Importance", *Pathol. Immunopathol. Res.*, 5, pp. 371–383 (1986).

Davis, M.M., et al., "Cell Type–Specific cDNA Probes and the Murine I Region: The Localization and Orientation of Ad", *Proc. Natl. Acad. Sci. USA*, 81, pp. 2194–2198 (1984).

Davis, M.M., "Subtractive cDNA Hybridization and the T–cell Receptor Gene", *Handbook of Experimental Immunology In Four Volumes*, 4th ed. Blackwell Scientific Publications, Oxford, England (1986), pp. 76.1–76.13.

Devereux, J., et al., "A Comprehensive Set of Sequence Analysis Programs for the VAX", *Nucl. Acids Res.*, 12, pp. 387–395 (1984).

Dixon, L., et al., "Evidence For Replicative Recombination In Cauliflower Mosaic Virus", *Virology*, 150, pp. 463–468 (1986).

Duguid, J.R., et al., "Isolation of cDNAs of Scrapie–Modulated RNAs by Subtractive Hybridization of a cDNA Library", *Proc. Natl. Acad. Sci. USA*, 85, pp. 5738–5742 (1988).

Dustin, M.L., et al., Induction by IL1 and Interferon–gamma: Tissue Distribution, Biochemistry, and Function of a Natural Adherence Molecule (ICAM–1), *J. Immunol.*, 137, pp. 245–254 (1986).

Dustin, M.L., and T.A. Springer, "Lymphocyte Function–Associated Antigen–1 (LFA–1) Interaction with Intercellular Adhesion Molecule 1 (ICAM1) Is One of at Least Three Mechanisms for Lymphocyte Adhesion to Cultured Endothelial Cells", *J. Cell. Biol.*, 107, pp. 321–333 (1988).

Elices, M.S., et al., "VCAM–1 on Activated Endothelium Interacts with the Leukocyte Integrin VLA–4 at a Site Distinct from the VLA–4 Fibronetin Binding Site", *Cell*, 60, p. 577–584 (1990).

Ellison, J.W., et al., "The Sequence of a Human Immunoglobulin C–gamma–1 Gene", *Nucl. Acids Res.*, 10, pp. 4071–4079 (1982).

Feinberg, A.P., and B. Vogelstein, "A Technique for Radiolabeling DNA Restriction Endonuclease Fragments to High Specific Activity", *Anal. Biochem.*, 132, pp. 6–13 (1983).

Feinberg, A.P., and B. Vogelstein, "A Technique for Radiolabeling DNA Restriction Endonuclease Fragments to High Specific Activity", *Anal. Biochem.*, 137, pp. 266–267 (1984).

Fisher, R.A., et al., "HIV Infection Is Blocked In Vitro by Recombinant Soluble CD4", *Nature*, 331, pp. 76–78 (1988).

Gimbrone, M.A., "Culture of Vascular Endothelium", *Prog. Hemostasis Thromb.*, 3, pp. 1–28 (1976).

Goldenberg, D.M., "Targeted Cancer Treatment", *Immunology Today*, 10, pp. 286–288 (1989).

Grau, G.E., et al., "Monoclonal Antibody Against Interferon Gamma Can Prevent Experimental Cerebral Malaria and Its Associated Overproduction of Tumor Necrosis Factor", *Proc. Natl. Acad. Sci., USA*, 86, pp. 5572–5574 (1989).

Gubler, U. and Hoffman, B.J., "A Simple and Very Efficient Method for Generating cDNA Libraries", *Gene*, 25, pp. 263–269 (1983).

Hambor, J.E., et al., "Functional Consequences of Anti–Sense RNA–Mediated Inhibition of CD8 Surface Expression in a Human T Cell Clone", *J. Exp. Med.*, 168, pp. 1237–1245 (1988).

Harlan, J.M., et al., "The Role of Neutrophil Membrane Proteins in Neutrophil Emigration", in *Leukocyte Emigration and Its Sequelae*, H. Movat, ed. (S. Karger AG, Basel, Switzerland, 1987), pp. 94–104.

Harlan, J.M., "Neutrophil–Mediated Vascular Injury", *Acta Med. Scand.*, Suppl., 715, pp. 123–129 (1987).

Harlan, J.M., "Leukocyte–Endothelial Interactions", *Blood*, 65, pp. 513–525 (1985).

Haselhoff, J., and W.L. Gerlach, "Simple RNA Enzymes with New and Highly Specific Endoribonuclease Activities", *Nature*, 334, pp. 585–591 (1988).

Hedrick, S.M., et al., "Isolation of cDNA Clones Encoding T Cell–Specific Membrane–Associated Proteins", *Nature*, 308, pp. 149–153 (1984).

Hemler, M.E., et al., "The VLA Protein Family (Characterization of Five Distinct Cell Surface Heterodimers Each with a Common 130,000 Molecular Weight Subunit)", *J. Biol. Chem.*, 262, pp. 3300–3309 (1987a).

Hemler, M.E., et al., "Characterization of the Cell Surface Heterodimer VLA–4 and Related Peptides", *J. Biol. Chem.*, 262, pp. 11478–11485 (1987b).

Hemler, M.E., "Adhesion Protein Receptors on Hematopoietic Cells", *Immunol. Today*, 9, pp. 109–113 (1988).

Hession, C., et al., "Endothelial Leukocyte Adhesion Molecule 1: Direct Expression Cloning and Functional Interactions", *Proc. Natl. Acad. Sci., USA*, 87, pp. 1673–1677 (1990).

Hirt, B., "Selective Extraction of Polyoma DNA from Infected Mouse Cell Cultures", *J. Mol. Biol.*, 26, pp. 365–369 (1967).

Hough, A. and L. Sokoloff, "Pathology", Chap. 4, *Rheumatoid Arthritis*, P.D. Ustinger, N.J. Zugifler, and Ehrlich, G.E., eds., (Lippencott, Philadelphia, 1985), pp. 49–69.

Hunkapiller, T. and L. Hood, "Diversity of the Immunoglobulin Gene Superfamily", *Adv. Immunol.*, 44, pp. 1–63 (1989).

Huse, W.D., et al., "Generation of a Large Combinatorial Library of the Immunoglobulin Repertoire in Phage Lambda", *Science*, 246, pp. 1275–1281 (1989).

Hynes, R.O., "Integrins: A Family of Cell Surface Receptors", *Cell*, 48, pp. 549–554 (1987).

Kalderon et al., "Deletion Loop Mutagenesis: A Novel Method for the Construction of Point Mutations Using Deletion Mutants", *Nucl. Acids Res.*, 10, pp. 5161–5171 (1982).

Kennedy, R.C., et al., "Anti–idiotypes and Immunity", *Sci. Am.*, 255, pp. 48–56 (Jul. 1986).

Kukowska–Latallo, J.F., et al., "A Cloned Human cDNA Determines Expression of a Mouse Stage–specific Embryonic Antigen and the Lewis Blood Group α(1,3/1,4)Fucosyltransferase", *Genes and Development*, 4, pp. 1288–1303 (1990).

Kurzinger, K., et al., "A Novel Lymphocyte Function–Associated Antigen (LFA–1): Cellular Distribution, Quantitative Expression, and Structure", *J. Immunol.,* 127, pp. 596–602 (1981).

Larsen, R.D., et al., "Molecular Cloning, Sequence, and Expression of a Human GPD–L–Fucose: –D–Galactoside 2–α–L–Fucosyltransferase cDNA That Can Form the H Blood Group Antigen", *Proc. Natl. Acad. Sci. USA,* 87, pp. 6674–6678 (1990).

Lehrach, H., et al., "RNA Molecular Weight Determinations by Gel Electrophoresis under Denaturing Conditions, a Critical Reexamination", *Biochem.,* 16, pp. 4743–4751 (1977).

Lenardo, M.J. and D. Baltimore, "NF–KB: A Pleiotropic Mediator of Inducible and Tissue Specific Gene Control", *Cell,* 58, pp. 227–230 (1989).

Lowe, J.B., et al., "ELAM–1 Dependent Cell Adhesion to Vascular Endothelium Determined by a Transfected Human Fucosyl–Transferase cDNA", *Cell,* 63, pp. 475–484 (1990).

Lundwall, A.B., et al., "Isolation and Sequence Analysis of a cDNA Clone Encoding The Fifth Complement Component", *J. Biol. Chem.,* 260, pp. 2108–2112 (1985).

Luscinskas, F.E., et al., "Endothelial–Leukocyte Adhesion Molecule–1 Dependent and Leukocyte (CD11/CD18) Dependent Mechanisms Contribute to Polymorphonuclear Leukocyte Adhesion to Cytokine Activated Human Vascular Epithelium", *J. Immunol.,* 142(7), pp. 2257–2263 (1989).

Malech, H.L. and Gallin, J.I., "Neutrophils in Human Diseases", *N. Eng. J. Med.,* 317, pp. 687–694 (1987).

Marcantonio, E.E., and R.O. Hynes, "Antibodies to the Conserved Cytoplasmic Domain of the Integrin β–1 Subunit React with Proteins in Vertebrates, Invertebrates and Fungi", *J. Cell. Biol,* 106, pp. 1765–1772 (1988).

Marcus–Sekura, C.J., "Techniques for Using Antisense Oligonucleotides to Study Gene Expression", *Anal. Biochem.,* 172, pp. 289–295 (1988).

Marlin, S.D., and T.A. Springer, "Purified Intercellular Adhesion Molecule–1 (ICAM–1) Is a Ligand for Lymphocyte Function–Associated Antigen 1 (LFA–1)", *Cell,* 51, pp. 813–819 (1987).

Maxam, A. and W. Gilbert, "Sequencing End–Labeled DNA with Base–Specific Chemical Cleavages", *Methods in Enzymol.,* 65, pp. 499–560 (1980).

Mohamed, A.H., et al., "Primary Structure of the Multifunctional α–Subunit Protein of Yeast Fatty Acid Synthase Derived from FAS2 Gene Sequence", *J. Biol. Chem.,* 263, pp. 12315–12325 (1988).

Morinaga et al., "Improvement of Oligonucleotide–Directed Site–Specific Mutagenesis Using Double–Stranded Plasmid DNA", *Bio/Technology,* 2, pp. 636–639 (1984).

Oostra et al., "Transforming Activity of Polyoma Virus Middle–T Antigen Probed by Site–Directed Mutagenesis", *Nature,* 304, pp. 456–460 (1983).

Osborn, L., et al., "Tumor Necrosis Factor α and Interleukin 1 Stimulate the Human Immunodeficiency Virus Enhancer by Activation of the Nucleus Factor κB", *Proc. Natl. Acad. Sci., U.S.A.,* 86, pp. 2336–2340 (1989).

Osborn, et al., "Direct Expression Cloning of Vascular Cell Adhesion Molecule 1, A Cytokine–Induced Endothelial Protein that Binds to Lymphocytes", *Cell,* 59, pp. 1203–1212 (1989).

Palcic, M.M., et al., "A Bisubstrate Analogue Inhibitor for α (1–2)–Fucosyltransferase", *J. Biol. Chem.,* 264, pp. 17177–17178 (1989).

Paulson, J.C., and K.J. Colley, "Glycosyltransferases: Structure, Localization, and Control of Cell Type–specific Glycosylation", *J. Biol. Chem.,* 264, pp. 17615–17618 (1989).

Peden, K.W.C. and D. Nathans, "Local Mutagenesis Within Deletion Loops of DNA Heteroduplexes", *Proc. Natl. Acad. Sci.,* U.S.A., 79, 7214–17 (1982).

Pober, J.S., et al., "Overlapping Patterns of Activation of Human Endothelial Cells by Interleukin 1, Tumor Necrosis Factor, and Immune Interferon", *J. Immunol.,* 137, pp. 1895–1896 (1986).

Potvin, B., et al., "Transfection of a Human alpha–(1,3) Fucosyltransferase Gene Into Chinese Hamster Ovary Cells", *J. Biol. Chem.,* 265, pp. 1615–1616 (1990).

Ross, R., "The Pathogenesis of Atherosclerosis—An Update", *N. Eng. J. Med,* 314, pp. 488–500 (1986).

Rothlein, R., et al., "A Human Intercellular Adhesion Molecule (ICAM–1) Distinct from LFA–1", *J. Immunol.,* 137, pp. 1270–1274 (1986).

Ruoslahti, E., "Fibronectin and its Receptors", *Ann. Rev. Biochem.,* 57, pp. 375–413 (1988).

Sambrook, J., et al., "In Vitro Amplification of DNA by Polymerase Chain Reaction", Chapter 14 in *Molecular Cloning, A Laboratory Manual,* Cold Spring Harbor Laboratory Press, Cold Spring Harbor, New York (1989).

Sandri–Goldin, R.M., et al., "High Frequency Transfer of Cloned Herpes Simplex Virus Type I Sequences to Mammalian Cells by Protoplast Fusion", *Molec. and Cell Biol.,* 1, pp. 743–752 (1981).

Sargent, T.D., "Isolation of Differentially Expressed Genes", *Methods in Enzymol.,* 152, pp. 423–447 (1987).

Sato, K., et al., "A Specific DNA Sequence Controls Termination of Transcription in the Gastrin Gene", *Molec. and Cell Biol.,* 6, pp. 1032–1043 (1986).

Schneider, C., et al., "A One–Step Purification of Membrane Proteins Using a High Efficiency Immunomatrix" *J. Biol. Chem.,* 257, pp. 10766–10769 (1982).

Schwartz, B.R., et al., "Identification of Surface Proteins Mediating Adherence of CD11/CD18—Deficient Lymphoblastoid Cells to Cultured Human Endothelium", *J. Clin. Invest.,* 85, pp. 2019–2022 (1990).

Seed, B., "An LFA–3 cDNA Encodes a Phospholipid–Linked Membrane Protein Homologous to Its Receptor CD2", *Nature,* 329, pp. 840–842 (1987).

Seed, B. and A. Aruffo, "Molecular Cloning of the CD2 Antigen, the T–cell Erythrocyte Receptor, by a Rapid Immunoselection Procedure", *Proc. Natl. Acad. Sci. USA,* 84, pp. 3365–3369 (1987).

Simmons et al., "ICAM, an Adhesion Ligand of LFA–1, Is Homologous to the Neural Cell Adhesion Molecule NCAM", *Nature,* 331, pp. 624–647 (1988).

Skerra, A. and A. Pluckthun, "Assembly of a Functional Immunoglobulin F▼ Fragment in *Escherichia coli*", *Science,* 240, pp. 1038–1043 (1988).

Smith, C.W., et al., "Cooperative Interactions of LFA–1 and Mac–1 with Intercellular Adhesion Molecule 1 in Facilitating Adherence and Transendothelial Cell Migration of Human Neutrophils in Vitro", *J. Clin. Invest.,* 83, pp. 2008–2017 (1989).

Springer, T.A., et al., "The Lymphocyte Function–Associated LFA–1, CD2, and LFA–3 Molecules: Cell Adhesion Receptors of the Immune System", *Ann. Rev. Immunol.,* 5, pp. 223–252 (1987).

Staunton, D.E., et al., "Primary Structure of ICAM–1 Demonstrates Interaction Between Members of the Immunoglobulin and Integrin Supergene Families", *Cell,* 52, pp. 925–933 (1988).

Subramani, S., et al., "Expression of the Mouse Dihydrofolate Reductase Complementary Deoxyribonucleic Acid in Simian Virus 40 Vectors", *Molec. Cell. Biol.,* 1, pp. 854–864 (1981).

Takada, Y., and M.E. Hemler, "The Primary Structure of the VLA–2/Collagen Receptor $\alpha^2$ Subunit (Platelet GP Ia): Homology to Other Integrins and the Presence of a Possible Collagen–Binding Domain", *J. Cell. Biol.,* 109, pp. 397–407 (1989).

Takada, Y., et al., "The Primary Structure of the α4 Subunit of VLA–4: Homology to Other Integrins and a Possible Cell–Cell Adhesion Function", *EMBO J.,* 8, pp. 1361–1368 (1989).

Thomas, H. and Sikora, K., "Biological Approaches to Cancer Therapy", *J. Intl. Med. Res.,* 17, pp. 191–204 (1989).

Todd III, R.F., et al., "The Anti–Inflammatory Properties of Monoclonal Anti–Mol (CD11B/CD18) Antibodies in Vitro and in Vivo", in *Structure and Function of Molecules Involved in Leukocyte Adhesion,* Chapter 9, pp. 125–137 Rosenthal et al., Eds., Springer–Verlag, New York (1989).

Vedder, N.B., et al., "A Monoclonal Antibody to the Adherence–Promoting Leukocyte Glycoprotein, CD18, Reduces Organ Injury and Improves Survival from Hemorrhagic Shock and Resuscitation in Rabbits", *J. Clin. Invest.,* 81, pp. 939–944 (1988).

von Heijne, G., "A Method for Predicting Signal Sequence Cleavage Sites", *Nucl. Acids Res.,* 14, pp. 4693–4690 (1986).

Wallis, W.J., and J.M. Harlan, "Effector Functions of Endothelium in Inflammatory and Immunologic Reactions", *Pathol. Immunopathol. Res.,* 5, pp. 73–103 (1986).

Walz, G., et al., "Recognition by ELAM–1 of the Sialyl–Le$^x$ Determinant on Myeloid and Tumor Cells", *Science,* 250, pp. 1132–1135 (1990).

Ward, E.S., et al., "Binding Activities of a Repertoire of Single Immunoglobulin Variable Domains Secreted from *Escherichia coli*", *Nature,* 341, pp. 544–546 (1989).

Warrick, H.M., et al., "Conserved Protein Domains in a Myosin Heavy Chain Gene From *Dictyostelium Discoideum*", *Proc. Natl. Acad. Sci.,* USA, 83, pp. 9433–9437 (1986).

Wayner, E.A., et al., "Identification and Characterization of the Lymphocyte Adhesion Receptor for an Alternative Cell Attachment Domain in Plasma Fibronectin", *J. Cell. Biol.,* in press (1989).

Weintraub, H.M., "Antisense RNA and DNA", *Sci. Am.,* 262, pp. 40–46 (Jan. 1990).

Wheeler, M.E., et al., "Cultured Human Endothelial Cells Stimulated with Cytokines or Endotoxin Produce an Inhibitor of Leukocyte Adhesion", *J. Clin. Invest.,* 82, pp. 1211–1218 (1988).

White, J. and D. Littman, "Viral Receptors of the Immunoglobulin Superfamily", *Cell,* 56, pp. 725–728 (1989).

Williams, A. and Barclay, A.N., "The Immunoglobulin Superfamily—Domains for Cell Surface Recognition", *Ann. Rev. Immunol.,* 6, pp. 381–405 (1988).

Wong, C.–H., "Enzymatic Catalysts in Organic Synthesis", *Science,* 244, pp. 1145–1152 (1989).

Wysocki, L.J. and V.L. Sato, "'Panning' for Lymphocytes: A Method for Cell Selection", *Proc. Natl. Acad. Sci. USA,* 75, pp. 2844–2848 (1978).

Yamasaki, K., et al., "Cloning and Expression of the Human Interleukin–6 (BSF–2/IFNB2) Receptor", *Science,* 241, pp. 825–828 (1988).

Young, R.A. and R.W. Davis, "Efficient Isolation of Genes by Using Antibody Probes", *Proc. Natl. Acad. Sci. USA,* 80, pp. 1194–1198 (1983).

Young, R.A. and R.W. Davis, "Yeast RNA Polymerase II Genes: Isolation with Antibody Probes", *Science,* 222, pp. 778–782 (1984).

Rice et al. An Inducible Endothelial Cell Surface Glycoprotein Mediates Melanoma Adhesion. Science 246:1303–1306, 1989.*

Pepinsky et al. Structure/Function Studies on Vascular Cell Adhesion Molecule–1. The Journal of Biological Chemistry. 267(25):17820–17826, 1992.*

All Other References of Record: See 1449, 892.*

Polte et al. Nuc. Acids Research 18:5901 (1990).*

Graber et al. J. Immunol 145:819–830 (1990).*

* cited by examiner

FIG. 1A

```
  1 TTCACATCAAAACTCCTATACTGACCTGAGACAGAGGCAGCAGTGATACC   50

51 CACCTGAGAGATCCTGTGTTTGAACAACTGCTTCCCAAAACGGAAAGTAT  100

101 TTCAAGCCTAAACCTTTGGGTGAAAGAACTCTTGAAGTCATGATTGCTT   150
                                          MetIleAlaS

151 CACAGTTTCTCTCAGCTCTCACTTTGGTGCTTCTCATTAAAGAGAGTGGA  200
    erGlnPheLeuSerAlaLeuThrLeuValLeuLeuIleLysGluSerGly

201 GCCTGGTCTTACAACACCTCCACGGAAGCTATGACTTATGATGAGGCCAG  250
    AlaTrpSerTyrAsnThrSerThrGluAlaMetThrTyrAspGluAlaSe

251 TGCTTATTGTCAGCAAAGGTACACACACCTGGTTGCAATTCAAAACAAAG  300
    rAlaTyrCysGlnGlnArgTyrThrHisLeuValAlaIleGlnAsnLysG

301 AAGAGATTGAGTACCTAAACTCCATATTGAGCTATTCACCAAGTTATTAC  350
    luGluIleGluTyrLeuAsnSerIleLeuSerTyrSerProSerTyrTyr

351 TGGATTGGAATCAGAAAAGTCAACAATGTGTGGGTCTGGGTAGGAACCCA  400
    TrpIleGlyIleArgLysValAsnAsnValTrpValTrpValGlyThrGl

401 GAAACCTCTGACAGAAGAAGCCAAGAACTGGGCTCCAGGTGAACCCAACA  450
    nLysProLeuThrGluGluAlaLysAsnTrpAlaProGlyGluProAsnA

451 ATAGGCAAAAAGATGAGGACTGCGTGGAGATCTACATCAAGAGAGAAAAA  500
    snArgGlnLysAspGluAspCysValGluIleTyrIleLysArgGluLys

501 GATGTGGGCATGTGGAATGATGAGAGGTGCAGCAAGAAGAAGCTTGCCCT  550
    AspValGlyMetTrpAsnAspGluArgCysSerLysLysLysLeuAlaLe

551 ATGCTACACAGCTGCCTGTACCAATACATCCTGCAGTGGCCACGGTGAAT  600
    uCysTyrThrAlaAlaCysThrAsnThrSerCysSerGlyHisGlyGluC

601 GTGTAGAGACCATCAATAATTACACTTGCAAGTGTGACCCTGGCTTCAGT  650
    ysValGluThrIleAsnAsnTyrThrCysLysCysAspProGlyPheSer

651 GGACTCAAGTGTGAGCAAATTGTGAACTGTACAGCCCTGGAATCCCCTGA  700
    GlyLeuLysCysGluGlnIleValAsnCysThrAlaLeuGluSerProGl

701 GCATGGAAGCCTGGTTTGCAGTCACCCACTGGGAAACTTCAGCTACAATT  750
    uHisGlySerLeuValCysSerHisProLeuGlyAsnPheSerTyrAsnS

751 CTTCCTGCTCTATCAGCTGTGATAGGGGTTACCTGCCAAGCAGCATGGAG  800
    erSerCysSerIleSerCysAspArgGlyTyrLeuProSerSerMetGlu
```

FIG. 1B

```
 801 ACCATGCAGTGTATGTCCTCTGGAGAATGGAGTGCTCCTATTCCAGCCTG  850
     ThrMetGlnCysMetSerSerGlyGluTrpSerAlaProIleProAlaCy
 851 CAATGTGGTTGAGTGTGATGCTGTGACAAATCCAGCCAATGGGTTCGTGG  900
     sAsnValValGluCysAspAlaValThrAsnProAlaAsnGlyPheValG
 901 AATGTTTCCAAAACCCTGGAAGCTTCCCATGGAACACAACCTGTACATTT  950
     luCysPheGlnAsnProGlySerPheProTrpAsnThrThrCysThrPhe
 951 GACTGTGAAGAAGGATTTGAACTAATGGGAGCCCAGAGCCTTCAGTGTAC 1000
     AspCysGluGluGlyPheGluLeuMetGlyAlaGlnSerLeuGlnCysTh
1001 CTCATCTGGGAATTGGACAACGAGAAGCCAACGTGTAAAGCTGTGACAT  1050
     rSerSerGlyAsnTrpAspAsnGluLysProThrCysLysAlaValThrC
1051 GCAGGGCCGTCCGCCAGCCTCAGAATGGCTCTGTGAGGTGCAGCCATTCC 1100
     ysArgAlaValArgGlnProGlnAsnGlySerValArgCysSerHisSer
1101 CCTGCTGGAGAGTTCACCTTCAAATCATCCTGCAACTTCACCTGTGAGGA 1150
     ProAlaGlyGluPheThrPheLysSerSerCysAsnPheThrCysGluGl
1151 AGGCTTCATGTTGCAGGGACCAGCCCAGGTTGAATGCACCACTCAAGGGC 1200
     uGlyPheMetLeuGlnGlyProAlaGlnValGluCysThrThrGlnGlyG
1201 AGTGGACACAGCAAATCCCAGTTTGTGAAGCTTTCCAGTGCACAGCCTTG 1250
     lnTrpThrGlnGlnIleProValCysGluAlaPheGlnCysThrAlaLeu
1251 TCCAACCCCGAGCGAGGCTACATGAATTGTCTTCCTAGTGCTTCTGGCAG 1300
     SerAsnProGluArgGlyTyrMetAsnCysLeuProSerAlaSerGlySe
1301 TTTCCGTTATGGGTCCAGCTGTGAGTTCTCCTGTGAGCAGGGTTTTGTGT 1350
     rPheArgTyrGlySerSerCysGluPheSerCysGluGlnGlyPheValL
1351 TGAAGGGATCCAAAAGGCTCCAATGTGGCCCCACAGGGGAGTGGGACAAC 1400
     euLysGlySerLysArgLeuGlnCysGlyProThrGlyGluTrpAspAsn
1401 GAGAAGCCCACATGTGAAGCTGTGAGATGCGATGCTGTCCACCAGCCCC  1450
     GluLysProThrCysGluAlaValArgCysAspAlaValHisGlnProPr
1451 GAAGGGTTTGGTGAGGTGTGCTCATTCCCTATTGGAGAATTCACCTACA  1500
     oLysGlyLeuValArgCysAlaHisSerProIleGlyGluPheThrTyrL
1501 AGTCCTCTTGTGCCTTCAGCTGTGAGGAGGGATTTGAATTACATGGATCA 1550
     ysSerSerCysAlaPheSerCysGluGluGlyPheGluLeuHisGlySer
1551 ACTCAACTTGAGTGCACATCTCAGGGACAATGGACAGAAGAGGTTCCTTC 1600
     ThrGlnLeuGluCysThrSerGlnGlyGlnTrpThrGluGluValProSe
```

FIG. IC

```
1601  CTGCCAAGTGGTAAAATGTTCAAGCCTGGCAGTTCCGGGAAAGATCAACA  1650
      rCysGlnValValLysCysSerSerLeuAlaValProGlyLysIleAsnM
1651  TGAGCTGCAGTGGGGAGCCCGTGTTTGGCACTGTGTGCAAGTTCGCCTGT  1700
      etSerCysSerGlyGluProValPheGlyThrValCysLysPheAlaCys
1701  CCTGAAGGATGGACGCTCAATGGCTCTGCAGCTCGGACATGTGGAGCCAC  1750
      ProGluGlyTrpThrLeuAsnGlySerAlaAlaArgThrCysGlyAlaTh
1751  AGGACACTGGTCTGGCCTGCTACCTACCTGTGAAGCTCCCACTGAGTCCA  1800
      rGlyHisTrpSerGlyLeuLeuProThrCysGluAlaProThrGluSerA
1801  ACATTCCCTTGGTAGCTGGACTTTCTGCTGCTGGACTCTCCCTCCTGACA  1850
      snIleProLeuValAlaGlyLeuSerAlaAlaGlyLeuSerLeuLeuThr
1851  TTAGCACCATTTCTCCTCTGGCTTCGGAAATGCTTACGGAAAGCAAAGAA  1900
      LeuAlaProPheLeuLeuTrpLeuArgLysCysLeuArgLysAlaLysLy
1901  ATTTGTTCCTGCCAGCAGCTGCCAAAGCCTTGAATCAGATGGAAGCTACC  1950
      sPheValProAlaSerSerCysGlnSerLeuGluSerAspGlySerTyrG
1951  AAAAGCCTTCTTACATCCTTTAAGTTCAAAAGAATCAGAAACAGGTGCAT  2000
      lnLysProSerTyrIleLeu
2001  CTGGGGAACTAGAGGGATACACTGAAGTTAACAGAGACAGATAACTCTCC  2050
2051  TCGGGTCTCTGGCCCTTCTTGCCTACTATGCCAGATGCCTTTATGGCTGA  2100
2101  AACCGCAACACCCATCACCACTTCAATAGATCAAAGTCCAGCAGGCAAGG  2150
2151  ACGGCCTTCAACTGAAAAGACTCAGTGTTCCCTTTCCTACTCTCAGGATC  2200
2201  AAGAAAGTGTTGGCTAATGAAGGGAAAGGATATTTTCTTCCAAGCAAAGG  2250
2251  TGAAGAGACCAAGACTCTGAAATCTCAGAATTCCTTTTCTAACTCTCCCT  2300
2301  TGCTCGCTGTAAAATCTTGGCACAGAAACACAATATTTTGTGGCTTTCTT  2350
2351  TCTTTTGCCCTTCACAGTGTTTCGACAGCTGATTACACAGTTGCTGTCAT  2400
2401  AAGAATGAATAATAATTATCCAGAGTTTAGAGGAAAAAAATGACTAAAAA  2450
2451  TATTATAACTTAAAAAATGACAGATGTTGAATGCCCACAGGCAAATGCAT  2500
2501  GGAGGGTTGTTAATGGTGCAAATCCTACTGAATGCTCTGTGCGAGGGTTA  2550
2551  CTATGCACAATTTAATCACTTTCATCCCTATGGATTCAGTGCTTCTTAA   2600
```

FIG. 1D

```
2601  AGAGTTCTTAAGGATTGTGATATTTTACTTGCATTGAATATATTATAAT  2650
2651  CTTCCATACTTCTTCATTCAATACAAGTGTGGTAGGGACTTAAAAAACTT  2700
2701  GTAAATGCTGTCAACTATGATATGGTAAAAGTTACTTATTCTAGATTACC  2750
2751  CCCTCATTGTTTATTAACAAATTATGTTACATCTGTTTTAAATTTATTTC  2800
2801  AAAAAGGGAAACTATTGTCCCCTAGCAAGGCATGATGTTAACCAGAATAA  2850
2851  AGTTCTGAGTGTTTTACTACAGTTGTTTTTGAAAACATGGTAGAATTG    2900
2901  GAGAGTAAAACTGAATGGAAGGTTTGTATATTGTCAGATATTTTTCAG    2950
2951  AAATATGTGGTTTCCACGATGAAAACTTCCATGAGGCCAAACGTTTTGA   3000
3001  ACTAATAAAGCATAAATGCAAACACACAAAGGTATAATTTATGAATGT    3050
3051  CTTTGTTGGAAAGAATACAGAAGATGGATGTGCTTTGCATTCCTACAA    3100
3101  AGATGTTTGTCAGATATGATATGTAAACATAATTCTTGTATATTATGGAA  3150
3151  GATTTAAATTCACAATAGAAACTCACCATGTAAAGAGTCATCTGGTAG    3200
3201  ATTTTAACGAATGAAGATGTCTAATAGTTATTCCCTATTTGTTTTCTTC   3250
3251  TGTATGTTAGGGTGCTCTGGAAGAGAGGAATGCCTGTGTGAGCAAGCATT  3300
3301  TATGTTTATTTATAAGCAGATTTAACAATTCCAAAGGAATCTCCAGTTTT  3350
3351  CAGTTGATCACTGGCAATGAAAAATTCTCAGTCAGTAATTGCCAAAGCTG  3400
3401  CTCTAGCCTTGAGGAGTGTGAGAATCAAAACTCTCCTACACTTCCATTAA  3450
3451  CTTAGCATGTGTTGAAAAAAAGTTTCAGAGAAGTTCTGGCTGAACACTG   3500
3501  GCAACAACAAAGCCAACAGTCAAAACAGAGATGTGATAAGGATCAGAACA  3550
3551  GCAGAGGTTCTTTTAAAGGGGCAGAAAACTCTGGGAAATAAGAGAGAAC   3600
3601  AACTACTGTGATCAGGCTATGTATGGAATACAGTGTTATTTCTTTGAAA   3650
3651  TTGTTTAAGTGTTGTAAATATTTATGTAAACTGCATTAGAAATTAGCTGT  3700
3701  GTGAAATACCAGTGTGGTTTGTGTTTGAGTTTATTGAGAATTTTAAATT   3750
3751  ATAACTTAAAATATTTTATAATTTTTAAAGTATATATTTATTTAAGCTTA  3800
```

FIG. IE

3801 TGTCAGACCTATTTGACATAACACTATAAAGGTTGACAATAAATGTGCTT 3850

3851 ATGTTTAAAAAAA 3863

```
  1  CGGGCCTCACTGGCTTCAGGAGCTGAATACCCTCCCAGGCACACACAGGT     50

51  GGGACACAAATAAGGGTTTTGGAACCACTATTTTCTCATCACGACAGCAA    100

101  CTTAAAATGCCTGGGAAGATGGTCGTGATCCTTGGAGCCTCAAATATACT    150
         MetProGlyLysMetValValIleLeuGlyAlaSerAsnIleLe

151  TTGGATAATGTTTGCAGCTTCTCAAGCTTTTAAAATCGAGACCACCCCAG    200
     uTrpIleMetPheAlaAlaSerGlnAlaPheLysIleGluThrThrProG

201  AATCTAGATATCTTGCTCAGATTGGTGACTCCGTCTCATTGACTTGCAGC    250
     luSerArgTyrLeuAlaGlnIleGlyAspSerValSerLeuThrCysSer

251  ACCACAGGCTGTGAGTCCCCATTTTTCTCTTGGAGAACCCAGATAGATAG    300
     ThrThrGlyCysGluSerProPhePheSerTrpArgThrGlnIleAspSe

301  TCCACTGAATGGGAAGGTGACGAATGAGGGGACCACATCTACGCTGACAA    350
     rProLeuAsnGlyLysValThrAsnGluGlyThrThrSerThrLeuThrM

351  TGAATCCTGTTAGTTTTGGGAACGAACACTCTTACCTGTGCACAGCAACT    400
     etAsnProValSerPheGlyAsnGluHisSerTyrLeuCysThrAlaThr

401  TGTGAATCTAGGAAATTGGAAAAGGAATCCAGGTGGAGATCTACTCTTT     450
     CysGluSerArgLysLeuGluLysGlyIleGlnValGluIleTyrSerPh

451  TCCTAAGGATCCAGAGATTCATTTGAGTGGCCCTCTGGAGGCTGGGAAGC    500
     eProLysAspProGluIleHisLeuSerGlyProLeuGluAlaGlyLysP

501  CGATCACAGTCAAGTGTTCAGTTGCTGATGTATACCCATTTGACAGGCTG    550
     roIleThrValLysCysSerValAlaAspValTyrProPheAspArgLeu

551  GAGATAGACTTACTGAAAGGAGATCATCTCATGAAGAGTCAGGAATTTCT    600
     GluIleAspLeuLeuLysGlyAspHisLeuMetLysSerGlnGluPheLe

601  GGAGGATGCAGACAGGAAGTCCCTGGAAACCAAGAGTTTGGAAGTAACCT    650
     uGluAspAlaAspArgLysSerLeuGluThrLysSerLeuGluValThrP

651  TTACTCCTGTCATTGAGGATATTGGAAAAGTTCTTGTTTGCCGAGCTAAA    700
     heThrProValIleGluAspIleGlyLysValLeuValCysArgAlaLys

701  TTACACATTGATGAAATGGATTCTGTGCCCACAGTAAGGCAGGCTGTAAA    750
     LeuHisIleAspGluMetAspSerValProThrValArgGlnAlaValLy

751  AGAATTGCAAGTCTACATATCACCCAAGAATACAGTTATTTCTGTGAATC    800
     sGluLeuGlnValTyrIleSerProLysAsnThrValIleSerValAsnP
```

FIG. 3B

```
 801  CATCCACAAAGCTGCAAGAAGGTGGCTCTGTGACCATGACCTGTTCCAGC   850
      roSerThrLysLeuGlnGluGlyGlySerValThrMetThrCysSerSer

851  GAGGGTCTACCAGCTCCAGAGATTTTCTGGAGTAAGAAATTAGATAATGG   900
      GluGlyLeuProAlaProGluIlePheTrpSerLysLysLeuAspAsnGl

901  GAATCTACAGCACCTTTCTGGAAATGCAACTCTCACCTTAATTGCTATGA   950
      yAsnLeuGlnHisLeuSerGlyAsnAlaThrLeuThrLeuIleAlaMetA

951  GGATGGAAGATTCTGGAATTTATGTGTGTGAAGGAGTTAATTTGATTGGG   1000
      rgMetGluAspSerGlyIleTyrValCysGluGlyValAsnLeuIleGly

1001  AAAAACAGAAAGAGGTGGAATTAATTGTTCAAGCATTCCCTAGAGATCC    1050
      LysAsnArgLysGluValGluLeuIleValGlnAlaPheProArgAspPr

1051  AGAAATCGAGATGAGTGGTGGCCTCGTGAATGGGAGCTCTGTCACTGTAA   1100
      oGluIleGluMetSerGlyGlyLeuValAsnGlySerSerValThrValS

1101  GCTGCAAGGTTCCTAGCGTGTACCCCCTTGACCGGCTGGAGATTGAATTA   1150
      erCysLysValProSerValTyrProLeuAspArgLeuGluIleGluLeu

1151  CTTAAGGGGGAGACTATTCTGGAGAATATAGAGTTTTGGAGGATACGGA    1200
      LeuLysGlyGluThrIleLeuGluAsnIleGluPheLeuGluAspThrAs

1201  TATGAAATCTCTAGAGAACAAAAGTTTGGAAATGACCTTCATCCCTACCA   1250
      pMetLysSerLeuGluAsnLysSerLeuGluMetThrPheIleProThrI

1251  TTGAAGATACTGGAAAAGCTCTTGTTTGTCAGGCTAAGTTACATATTGAT   1300
      leGluAspThrGlyLysAlaLeuValCysGlnAlaLysLeuHisIleAsp

1301  GACATGGAATTCGAACCCAAACAAAGGCAGAGTACGCAAACACTTTATGT   1350
      AspMetGluPheGluProLysGlnArgGlnSerThrGlnThrLeuTyrVa

1351  CAATGTTGCCCCAGAGATACAACCGTCTTGGTCAGCCCTTCCTCCATCC    1400
      lAsnValAlaProArgAspThrThrValLeuValSerProSerSerIleL

1401  TGGAGGAAGGCAGTTCTGTGAATATGACATGCTTGAGCCAGGGCTTTCCT   1450
      euGluGluGlySerSerValAsnMetThrCysLeuSerGlnGlyPhePro

1451  GCTCCGAAAATCCTGTGGAGCAGGCAGCTCCCTAACGGGGAGCTACAGCC   1500
      AlaProLysIleLeuTrpSerArgGlnLeuProAsnGlyGluLeuGlnPr

1501  TCTTTCTGAGAATGCAACTCTCACCTTAATTTCTACAAAAATGGAAGATT   1550
      oLeuSerGluAsnAlaThrLeuThrLeuIleSerThrLysMetGluAspS

1551  CTGGGGTTTATTTATGTGAAGGAATTAACCAGGCTGGAAGAAGCAGAAAG   1600
      erGlyValTyrLeuCysGluGlyIleAsnGlnAlaGlyArgSerArgLys
```

FIG. 3C

```
1601  GAAGTGGAATTAATTATCCAAGTTACTCCAAAAGACATAAAACTTACAGC  1650
      GluValGluLeuIleIleGlnValThrProLysAspIleLysLeuThrAl
1651  TTTTCCTTCTGAGAGTGTCAAAGAAGGAGACACTGTCATCATCTCTTGTA  1700
      aPheProSerGluSerValLysGluGlyAspThrValIleIleSerCysT
1701  CATGTGGAAATGTTCCAGAAACATGGATAATCCTGAAGAAAAAGCGGAG  1750
      hrCysGlyAsnValProGluThrTrpIleIleLeuLysLysLysAlaGlu
1751  ACAGGAGACACAGTACTAAAATCTATAGATGGCGCCTATACCATCCGAAA  1800
      ThrGlyAspThrValLeuLysSerIleAspGlyAlaTyrThrIleArgLy
1801  GGCCCAGTTGAAGGATGCGGGAGTATATGAATGTGAATCTAAAAACAAAG  1850
      sAlaGlnLeuLysAspAlaGlyValTyrGluCysGluSerLysAsnLysV
1851  TTGGCTCACAATTAAGAAGTTTAACACTTGATGTTCAAGGAAGAGAAAAC  1900
      alGlySerGlnLeuArgSerLeuThrLeuAspValGlnGlyArgGluAsn
1901  AACAAAGACTATTTTCTCCTGAGCTTCTCGTGCTCTATTTTGCATCCTC  1950
      AsnLysAspTyrPheSerProGluLeuLeuValLeuTyrPheAlaSerSe
1951  CTTAATAATACCTGCCATTGGAATGATAATTTACTTTGCAAGAAAAGCCA  2000
      rLeuIleIleProAlaIleGlyMetIleIleTyrPheAlaArgLysAlaA
2001  ACATGAAGGGGTCATATAGTCTTGTAGAAGCACAGAAATCAAAAGTGTAG  2050
      snMetLysGlySerTyrSerLeuValGluAlaGlnLysSerLysVal
2051  CTAATGCTTGATATGTTCAACTGGAGACACTATTTATCTGTGCAAATCCT  2100
2101  TGATACTGCTCATCATTCCTTGAGAAAAACAATGAGCTGAGAGGCAGACT  2150
2151  TCCCTGAATGTATTGAACTTGGAAAGAAATGCCCATCTATGTCCCTTGCT  2200
2201  GTGAGCAAGAAGTCAAAGTAAAACTTGCTGCCTGAAGAACAGTAACTGCC  2250
2251  ATCAAGATGAGAGAACTGGAGGAGTTCCTTGATCTGTATATACAATAACA  2300
2301  TAATTTGTACATATGTAAAATAAAATTATGCCATAGCAAGATTGCTTAAA  2350
2351  ATAGCAACACTCTATATTTAGATTGTTAAAATAACTAGTGTTGCTTGGAC  2400
2401  TATTATAATTTAATGCATGTTAGGAAAATTTCACATTAATATTTGCTGAC  2450
2451  AGCTGACCTTTGTCATCTTTCTTCTATTTTATTCCCTTTCACAAAATTTT  2500
2501  ATTCCTATATAGTTTATTGACAATAATTTCAGGTTTTGTAAAGATGCCGG  2550
```

FIG. 3D

```
2551 GTTTTATATTTTTATAGACAAATAATAAGCAAAGGGAGCACTGGGTTGAC 2600
2601 TTTCAGGTACTAAATACCTCAACCTATGGTATAATGGTTGACTGGGTTTC 2650
2651 TCTGTATAGTACTGGCATGGTACGGAGATGTTTCACGAAGTTTGTTCATC 2700
2701 AGACTCCTGTGCAACTTTCCCAATGTGGCCTAAAAATGCAACTTCTTTTT 2750
2751 ATTTTCTTTTGTAAATGTTTAGGTTTTTTTGTATAGTAAAGTGATAATTT 2800
2801 CTGGAATTAAA 2811
```

FIG. 4A

```
  1 CACTGGCTTCAGGAGCTGAATACCCTCCCAGGCACACACAGGTGGGACAC   50

51 AAATAAGGGTTTTGGAACCACTATTTTCTCATCACGACAGCAACTTAAAA  100
                                                     M
101 TGCCTGGGAAGATGGTCGTGATCCTTGGAGCCTCAAATATACTTTGGATA  150
    etProGlyLysMetValValIleLeuGlyAlaSerAsnIleLeuTrpIle

151 ATGTTTGCAGCTTCTCAAGCTTTTAAAATCGAGACCACCCCAGAATCTAG  200
    MetPheAlaAlaSerGlnAlaPheLysIleGluThrThrProGluSerAr

201 ATATCTTGCTCAGATTGGTGACTCCGTCTCATTGACTTGCAGCACCACAG  250
    gTyrLeuAlaGlnIleGlyAspSerValSerLeuThrCysSerThrThrG

251 GCTGTGAGTCCCCATTTTTCTCTTGGAGAACCCAGATAGATAGTCCACTG  300
    lyCysGluSerProPhePheSerTrpArgThrGlnIleAspSerProLeu

301 AATGGGAAGGTGACGAATGAGGGGACCACATCTACGCTGACAATGAATCC  350
    AsnGlyLysValThrAsnGluGlyThrThrSerThrLeuThrMetAsnPr

351 TGTTAGTTTTGGGAACGAACACTCTTACCTGTGCACAGCAACTTGTGAAT  400
    oValSerPheGlyAsnGluHisSerTyrLeuCysThrAlaThrCysGluS

401 CTAGGAAATTGGAAAAGGAATCCAGGTGGAGATCTACTCTTTTCCTAAG   450
    erArgLysLeuGluLysGlyIleGlnValGluIleTyrSerPheProLys

451 GATCCAGAGATTCATTTGAGTGGCCCTCTGGAGGCTGGGAAGCCGATCAC  500
    AspProGluIleHisLeuSerGlyProLeuGluAlaGlyLysProIleTh

501 AGTCAAGTGTTCAGTTGCTGATGTATACCCATTTGACAGGCTGGAGATAG  550
    rValLysCysSerValAlaAspValTyrProPheAspArgLeuGluIleA

551 ACTTACTGAAAGGAGATCATCTCATGAAGAGTCAGGAATTTCTGGAGGAT  600
    spLeuLeuLysGlyAspHisLeuMetLysSerGlnGluPheLeuGluAsp

601 GCAGACAGGAAGTCCCTGGAAACCAAGAGTTTGGAAGTAACCTTTACTCC  650
    AlaAspArgLysSerLeuGluThrLysSerLeuGluValThrPheThrPr

651 TGTCATTGAGGATATTGGAAAAGTTCTTGTTTGCCGAGCTAAATTACACA  700
    oValIleGluAspIleGlyLysValLeuValCysArgAlaLysLeuHisI

701 TTGATGAAATGGATTCTGTGCCCACAGTAAGGCAGGCTGTAAAAGAATTG  750
    leAspGluMetAspSerValProThrValArgGlnAlaValLysGluLeu
```

FIG. 4B

```
 751  CAAGTCTACATATCACCCAAGAATACAGTTATTTCTGTGAATCCATCCAC   800
      GlnValTyrIleSerProLysAsnThrValIleSerValAsnProSerTh

801  AAAGCTGCAAGAAGGTGGCTCTGTGACCATGACCTGTTCCAGCGAGGGTC   850
      rLysLeuGlnGluGlyGlySerValThrMetThrCysSerSerGluGlyL

851  TACCAGCTCCAGAGATTTTCTGGAGTAAGAAATTAGATAATGGGAATCTA   900
      euProAlaProGluIlePheTrpSerLysLysLeuAspAsnGlyAsnLeu

901  CAGCACCTTTCTGGAAATGCAACTCTCACCTTAATTGCTATGAGGATGGA   950
      GlnHisLeuSerGlyAsnAlaThrLeuThrLeuIleAlaMetArgMetGl

951  AGATTCTGGAATTTATGTGTGTGAAGGAGTTAATTTGATTGGGAAAAACA  1000
      uAspSerGlyIleTyrValCysGluGlyValAsnLeuIleGlyLysAsnA

1001  GAAAAGAGGTGGAATTAATTGTTCAAGAGAAACCATTTACTGTTGAGATC  1050
      rgLysGluValGluLeuIleValGlnGluLysProPheThrValGluIle

1051  TCCGCTGGACCCCGGATTGCTGCTCAGATTGGAGACTCAGTCATGTTGAC  1100
      SerProGlyProArgIleAlaAlaGlnIleGlyAspSerValMetLeuTh

1101  ATGTAGTGTCATGGGCTGTGAATCCCCATCTTTCTCCTGGAGAACCCAGA  1150
      rCysSerValMetGlyCysGluSerProSerPheSerTrpArgThrGlnI

1151  TAGACAGCCCTCTGAGCGGGAAGGTGAGGAGTGAGGGACCAATTCCACG   1200
      leAspSerProLeuSerGlyLysValArgSerGluGlyThrAsnSerThr

1201  CTGACCCTGAGCCCTGTGAGTTTTGAGAACGAACACTCTTATCTGTGCAC  1250
      LeuThrLeuSerProValSerPheGluAsnGluHisSerTyrLeuCysTh

1251  AGTGACTTGTGGACATAAGAAACTGGAAAAGGGAATCCAGGTGGAGCTCT  1300
      rValThrCysGlyHisLysLysLeuGluLysGlyIleGlnValGluLeuT

1301  ACTCATTCCCTAGAGATCCAGAAATCGAGATGAGTGGTGGCCTCGTGAAT  1350
      yrSerPheProArgAspProGluIleGluMetSerGlyGlyLeuValAsn

1351  GGGAGCTCTGTCACTGTAAGCTGCAAGGTTCCTAGCGTGTACCCCCTTGA  1400
      GlySerSerValThrValSerCysLysValProSerValTyrProLeuAs

1401  CCGGCTGGAGATTGAATTACTTAAGGGGGAGACTATTCTGGAGAATATAG  1450
      pArgLeuGluIleGluLeuLeuLysGlyGluThrIleLeuGluAsnIleG

1451  AGTTTTGGAGGATACGGATATGAAATCTCTAGAGAACAAAAGTTTGGAA   1500
      luPheLeuGluAspThrAspMetLysSerLeuGluAsnLysSerLeuGlu

1501  ATGACCTTCATCCCTACCATTGAAGATACTGGAAAAGCTCTTGTTTGTCA  1550
      MetThrPheIleProThrIleGluAspThrGlyLysAlaLeuValCysGl
```

FIG. 4C

```
1551 GGCTAAGTTACATATTGATGACATGGAATTCGAACCCAAACAAAGGCAGA 1600
     nAlaLysLeuHisIleAspAspMetGluPheGluProLysGlnArgGlnS
1601 GTACGCAAACACTTTATGTCAATGTTGCCCCAGAGATACAACCGTCTTG   1650
     erThrGlnThrLeuTyrValAsnValAlaProArgAspThrThrValLeu
1651 GTCAGCCCTTCCTCCATCCTGGAGGAAGGCAGTTCTGTGAATATGACATG 1700
     ValSerProSerSerIleLeuGluGluGlySerSerValAsnMetThrCy
1701 CTTGAGCCAGGGCTTTCCTGCTCCGAAAATCCTGTGGAGCAGGCAGCTCC 1750
     sLeuSerGlnGlyPheProAlaProLysIleLeuTrpSerArgGlnLeuP
1751 CTAACGGGGAGCTACAGCCTCTTTCTGAGAATGCAACTCTCACCTTAATT 1800
     roAsnGlyGluLeuGlnProLeuSerGluAsnAlaThrLeuThrLeuIle
1801 TCTACAAAAATGGAAGATTCTGGGGTTTATTTATGTGAAGGAATTAACCA 1850
     SerThrLysMetGluAspSerGlyValTyrLeuCysGluGlyIleAsnGl
1851 GGCTGGAAGAAGCAGAAAGGAAGTGGAATTAATTATCCAAGTTACTCCAA 1900
     nAlaGlyArgSerArgLysGluValGluLeuIleIleGlnValThrProL
1901 AAGACATAAAACTTACAGCTTTTCCTTCTGAGAGTGTCAAAGAAGGAGAC 1950
     ysAspIleLysLeuThrAlaPheProSerGluSerValLysGluGlyAsp
1951 ACTGTCATCATCTCTTGTACATGTGGAAATGTTCCAGAAACATGGATAAT 2000
     ThrValIleIleSerCysThrCysGlyAsnValProGluThrTrpIleIl
2001 CCTGAAGAAAAAGCGGAGACAGGAGACACAGTACTAAAATCTATAGATG   2050
     eLeuLysLysLysAlaGluThrGlyAspThrValLeuLysSerIleAspG
2051 GCGCCTATACCATCCGAAAGGCCCAGTTGAAGGATGCGGGAGTATATGAA 2100
     lyAlaTyrThrIleArgLysAlaGlnLeuLysAspAlaGlyValTyrGlu
2101 TGTGAATCTAAAAACAAAGTTGGCTCACAATTAAGAAGTTTAACACTTGA 2150
     CysGluSerLysAsnLysValGlySerGlnLeuArgSerLeuThrLeuAs
2151 TGTTCAAGGAAGAGAAAACAACAAAGACTATTTTCTCCTGAGCTTCTCG   2200
     pValGlnGlyArgGluAsnAsnLysAspTyrPheSerProGluLeuLeuV
2201 TGCTCTATTTTGCATCCTCCTTAATAATACCTGCCATTGGAATGATAATT 2250
     alLeuTyrPheAlaSerSerLeuIleIleProAlaIleGlyMetIleIle
2251 TACTTTGCAAGAAAGCCAACATGAAGGGGTCATATAGTCTTGTAGAAGC   2300
     TyrPheAlaArgLysAlaAsnMetLysGlySerTyrSerLeuValGluAl
2301 ACAGAAATCAAAAGTGTAGCTAATGCTTGATATGTTCAACTGGAGACACT 2350
     aGlnLysSerLysVal
```

FIG. 4D

```
2351  ATTTATCTGTGCAAATCCTTGATACTGCTCATCATTCCTTGAGAAAAACA  2400
2401  ATGAGCTGAGAGGCAGACTTCCCTGAATGTATTGAACTTGGAAAGAAATG  2450
2451  CCCATCTATGTCCCTTGCTGTGAGCAAGAAGTCAAAGTAAAACTTGCTGC  2500
2501  CTGAAGAACAGTAACTGCCATCAAGATGAGAACTGGAGGAGTTCCTTG    2550
2551  ATCTGTATATACAATAACATAATTTGTACATATGTAAAATAAAATTATGC  2600
2601  CATAGCAAGATTGCTTAAAATAGCAACACTCTATATTTAGATTGTTAAAA  2650
2651  TAACTAGTGTTGCTTGGACTATTATAATTTAATGCATGTTAGGAAAATTT  2700
2701  CACATTAATATTTGCTGACAGCTGACCTTTGTCATCTTTCTTCTATTTTA  2750
2751  TTCCCTTTCACAAAATTTTATTCCTATATAGTTTATTGACAATAATTTCA  2800
2801  GGTTTTGTAAAGATGCCGGGTTTTATATTTTTATAGACAAATAATAAGCA  2850
2851  AAGGGAGCACTGGGTTGACTTTCAGGTACTAAATACCTCAACCTATGGTA  2900
2901  TAATGGTTGACTGGGTTTCTCTGTATAGTACTGGCATGGTACGGAGATGT  2950
2951  TTCACGAAGTTTGTTCATCAGACTCCTGTGCAACTTTCCCAATGTGGCCT  3000
3001  AAAAATGCAACTTCTTTTTATTTTCTTTTGTAAATGTTTAGGTTTTTTG   3050
3051  TATAGTAAAGTGATAATTTCTGGAATTAAA  3080
```

FIG. 5

```
           G   h  E  C         P      Wp                      P  DsG  o C     N              P  DsG  o C     N
                *                                                   *
1                                FKIETTPESRYLAQIGDSVSLTCSTTGCESPFFSWRTQIDSPLNGK------------VTNEGTTSTLTHNPVSFGNEHSYLCTATCESRKLEKGI
2   QVEIYSFPKDPEIHLSGPL-EAGKPITVKCSVA-DVYPFDRLEIDLLKGDHLMKSQEFLEDADRKSLETKSLEVTFTPVIEDIGKVLVCRAKLHIDEMDSVPTVRQAVKEL
3   QVYISPKNTVISVNPSTKL-QEGGSVTMTCSSEGLPAPEIFVSKKLDNGNLQH-----------LSGNATLTL-IAMRHEDSG-IYVCEGVNLIGKNRKEVELIVQA
4   FPRDPEIEMSGGL-VNGSSVTVSCKVP-SVYPLDRLEIEILKGETILENIEFLEDTDMKSLENKSLEMTFIPTIEDTGKALVCQAKLHIDDHEFEPKQRQSTQTL
5   YVNVAPRDTTVLVSPSSIL-EEGSSVNMTCLSQGFPAPKILVSRQLPNGELQP-----------LSENATLTL-ISTKMEDSG-VYLCEGINQAGRSRKEVELIQV
6                        TPKDIKLTAFPSESV-KEGDTVIISCTCGNV---PET-WIILKKAETGDTVL---------SIDGAYTIRKAQLKDAG-VYECESKNKVGSQLRSLTLDVQGREN

NKDYFSPELLVLYFASSLIIPAIGMIIYFARKANMKGSYSLVEAQKSKV
```

FIG. 6

```
          *       G h f c    P   Wp                                                           P   DsG  o C   N                                        *
1                 FKIETTPESRYLAQIGDSVSLTCSTTGCESPFFSVRTQIDSPLNGK------------VTNEGTTSTLTMNPVSFGNEHSYLCTATCBSRKLEKGI
2    QVEIYSFPKDPEIHLSGPL-EAGKPITVKCSVA-DVYPEDRLEIDLLKGDBLMKSQEFLEDADRKSLETKSLEVTFTPVIEDIGKVLVCRAKLHIDEMDSVPTVRQAVKEL
3    QVYISPKNTVISVNPSTKL-QEGGSVTMTCSSEGLPAPEIFWSKKLDNGNLQH------------LSGNATLTL-IAMRMEDSG--IYVCEGVNLIGKNRKEVELIVQEKP
3B                FTVEISPGPRIAAQIGDSVMLTCSVHGCESPSFSVRTQIDSPLSGK------------VRSEGTNSTLTLSPVSFENEHSYLCTVTCGHKKLEKGI
4    QVELYSFPRDPEIEMSGGL-VNGSSVTVSCKVP-SVYPLDRLEIELLKGETILENIEFLEDTDHKSLEMTFIPTIEDTGKALVCQAKLHIDDMEFEPKQRQSTQTL
5    YVNVAPRDTTVLVSPSSIL-EEGSSVNMTCLSQGFPAPKILWSRQLPNGELQP------------LSENATLTL-ISTKMEDSG--VYLCEGINQAGRSRKEVELIIQV
6    TPKDIKLTAFPSESV-KEGDTVIISCTCGNV---PET-WIILKKKAETGDTVL------------SIDGAYTIRKAQLKDAG--VYBCESKNKVGSQLRSLTLDVQGREN

NKDYFSPELLVLYFASSLIIPAIGMIIYFARKANMKGSYSLVEAQKSKV
```

FIG. 7A

```
   1  GCATGCGCCA CCATGCCCAG CTAATTTTGT ATTTTTAGTA GAGATGGCGT
  51  TTCTCCATGT TGGTCAGGCT GGTCTTGAAC TCCCGGCCTC AGGTGATCCG
 101  CCTGCCTCGG CCTCCCAAAG TGGTGGGATT ACAGGCGTGA GCCACTGTGC
 151  CTGGCCTCCT TTTTATTTTT TTCACTGAAC AAACCATGAA ACTTTCCCAG
 201  ATGTAAATAT CTATTTCCCA TTTTTCTTTT TTTAAAATAA GGCATTATTT
 251  TAACCATTTG AGTGTTAGAT ATTATTTTTA GATAATATTT TAATTTAGGC
 301  ATAACTGCCG TGCAAAATCT GAAGATTAAT ATCTACCTTG TGAGTCATTC
 351  CTCTGTGAGA CAGTGCATGT TAAATATGTT GAATTGGCAG GTGAAAAAGG
 401  AAGAAAAAAT GAGTAGTGAT TGGTTATCCA CAGCTATGAA TGAGAAATTG
 451  AAGGTAGTAG ACTATGGATG ACAAACCTAT TCTTGGTTTC CTTCTGTTTC
 501  TGAAATTCTA ATTACTACCA CAACTACATG AGAGACACTA CTAACAAGCA
 551  AAGTTTTACA ACTTTTTAAA GACATAGACT TTATGTTATT ATAATTAAAA
 601  ATCATGCATT TTTGTCATAT TAATAAAATT GCATATACGA TATAAAGGCA
 651  TGGACAAAGG TGAAGTAGCT TCAAGAGACA GAGTTTCTGA CATCATTGTA
                                                              NF-
 701  ATTTTAAGCA TCGTGGATAT TCCCGGGAAA GTTTTTGGAT GCCATTGGGG
      kappaB
 751  ATTTCCTCTT TACTGGATGT GGACAATATC CTCCTATTAT TCACAGGAAG
 801  CAATCCCTCC TATAAAGGG CCTCAGCCGA AGTAGTGTTC AGCTGTTCTT
          cDNA clone 41
 851  GGCTGACTTC ACATCAAAAC TCCTATACTG ACCTGAGACA GAGGCAGCAG
                                                              in-
 901  TGATACCCAC CTGAGAGATC CTGTGTTTGA ACAACTGCTT CCCAAAACGG
      tron 1
 951  TAAGTGCAGA ACGCTTTATA AGGGCAGCCT CGGGCCATGA ACACAGATA
1001  TGCAAAAGGC CTTCTAATAA AAACCACATC TGTACAAGCT CTTATTGTAT
1051  TGTAGCTAAA .ACCTGTCTTT TCTCTTTGAC CTAAATAATG AAAGTCTTAA
1101  AAATTGTTTA TTTATTTGAT TAAACTCTGA AATAAAGATT ATTGCACTAG
1151  TGTCCTTTGC CCAAAATCTT AGGATGCTGC CTTAAACATC ATGGTAGAAT
```

FIG. 7B

```
1201 AATGTAACTA GCTACCCACG ATTTCCTTCT TTAATTCATT TTGTGTTTTA
              exon 2
1251 TCTCCCCAGG AAAGTATTTC AAGCCTAAAC CTTTGGGTGA AAAGAACTCT
             translation initiation codon
1301 TGAAGTCATG ATTGCTTCAC AGTTTCTCTC AGCTCTCACT TTGGGTAAGT
                                                   intron 2
1351 CAGTGCCATT AGACCAAGAT TTCTCATTCT CGCACTATAG ATATTTCAGA

1401 CTGAAATATC CTTGCTTGTC TGGGGCTGTC CTGCACAGGA TATCTGGCAG

1451 CATCCTTGAC CTCTACCTGC AATGTGTTCT TCCCTGGGCT TGGGGTCATT

1501 TACTTTACCT CTTGGTGTCT CCCTTTCCTT AAGTGTAAAG TGTGGATCCG

1551 TTGACCTGCA GGTCGA
```

VASCULAR CELL ADHESION MOLECULE (VCAM) POLYPEPTIDES

This application is a division of application Ser. No. 08/035,674, now U.S. Pat. No. 5,367,056, filed Mar. 23, 1993, as a division of application Ser. No. 07/452,675, now U.S. Pat. No. 5,272,263, filed Dec. 18, 1989, as a continuation-in-part of application Ser. No. 07/359,516, now abandoned, filed Jun. 1, 1989, as a continuation-in-part of application Ser. No. 07/345,151, filed Apr. 28, 1989, now U.S. Pat. No. 5,217,870.

TECHNICAL FIELD OF INVENTION

This invention relates to molecules involved in the adhesion of leukocytes to endothelial cells during inflammation and to DNA sequences that code on expression for them. More particularly, it relates to Endothelial Cell Adhesion Molecules (ELAMs), including ELAM1 and Vascular Cell Adhesion Molecule 1 and 1b (VCAM1 and VCAM1b). It also relates to molecules on the surface of leukocytes involved in leukocyte adhesion to endothelial cells (MILAs). These include CDX, a molecule involved in the ELAM1 adhesion pathway, and VLA4, the ligand of VCAM1 and VCAM1b. This invention further relates to antibodies that recognize these adhesion molecules and anti-idiotype antibodies that recognize both those antibodies and the ligands or receptors for the adhesion molecules. The invention also relates to antisense DNA and RNA molecules complementary to mRNA for such adhesion molecules and also relates to ribozymes which recognize mRNA for such molecules. The invention also relates to methods for using the aforementioned molecules, DNA sequences, antibodies, anti-idiotype antibodies, antisense molecules and ribozymes, for example in developing diagnostic and therapeutic agents to detect or inhibit leukocyte adhesion to endothelial cells.

BACKGROUND OF THE INVENTION

Inflammation is thee response of vascularized tissues to infection or injury. Clinically it is accompanied by four classic signs: redness, heat, pain and swelling. Its course may be acute or chronic.

At the cellular level, inflammation involves the adhesion of leukocytes (white blood cells) to the endothelial wall of blood vessels and their infiltration into the surrounding tissues. (Harlan, 1985.) Acute inflammation is characterized by the adhesion and infiltration of polytmorphonuclear leukocytes (PMNs). (Harlan, 1987 and Malech and Gallin, 1987.) PMN accumulation in the tissues reaches its peak between two and one half to four hours after an inflammatory stimulus and ceases by about twenty-eight hours (Bevilacqua and Gimbrone, 1987). In contrast, chronic inflammation is characterized by the adhesion and infiltration of other leukocytes, especially monocytes and lymphocytes.

In normal inflammation, the infiltrating leukocytes phagocytize invading organisms or dead cells, and play a role in tissue repair and the immune response. However, in pathologic inflammation, infiltrating leukocytes can cause serious and sometimes deadly damage. Rheumatoid arthritis and atherosclerosis are examples of chronic inflammatory diseases in which mononuclear leukocytes infiltrate the tissues and cause damage. (Hough and Sokoloff, 1985 and Ross, 1986.) Multiple organ failure syndrome, adult respiratory distress syndrome (ARDS), and ischemic reperfusion injury are acute inflammations in which infiltrating PMNs cause the damage (Harlan, 1987 and Malech and Gallin, 1987). In multiple organ failure syndrome, which can occur after shock such as that associated with severe burns, PMN-mediated damage exacerbates the injury. In ARDS, PMNs cause the lungs to fill with fluid, and the victim may drown. In ischemic reperfusion injury, which occurs when tissue cut off from the supply of blood is suddenly perfused with blood (for example after heart attack, stroke, or limb re-attachment), PMN adhesion causes serious tissue damage (Harlan, 1987).

Recognizing that leukocyte infiltration is the cause of much inflammation-related pathology and that leukocyte adhesion is the first step in infiltration, investigators have recently focused attention on the mechanism of leukocyte binding to the endothelial cell surface. Studies show that binding is mediated by cell-surface molecules on both endothelial cells and leukocytes which act as receptor and ligand (Harlan et al., 1987; Dana et al., 1986; and Bevilacqua et al., 1987a).

During the course of inflammation, certain inflammatory agents can act on the leukocytes, making them hyperadhesive for endothelium. Known inflammatory agents include leukotriene-B4 (LTB4), complement factor 5a (C5a), and formyl-methionyl-leucyl-phenylalanine (FMLP). These agents activate a group of proteins called LeuCAMs. The LeuCAMs are dimers of the CD11 and CD18 proteins. One of the LeuCAMs, CD11a/CD18 (also called LFA-1) binds to a receptor on endothelial cells called ICAM1 (intercellular adhesion molecule 1). (Harlan, 1985 and Dana et al., 1986.) Investigators have shown that monoclonal antibodies (Moabs) to LeuCAMs inhibit PMN adhesion to endothelium both in vitro and in vivo. (Arfors, 1987; Vedder et al., 1988; and Todd, 1989.)

Other inflammatory agents act directly on endothelial cells to substantially augment leukocyte adhesion. These agents include the cytokines interleukin-1 (IL-1), lymphotoxin (LT) and tumor necrosis factor (TNF), as well as the bacterial endotoxin, lipopolysaccharide (LPS). For example, IL1 has been shown to stimulate adhesion of PMNs, monocytes, and the related cell lines HL-60 (PMN-like) and U937 (monocyte-like), to human endothelial cell monolayers. The action is both time-dependent and protein-synthesis dependent. (Bevilaqcua et al., 1987a; Bevilacqua et al., 1987b; and Bevilacqua et al., 1985.)

Current evidence indicates that these agents induce a group of molecules on the endothelial cell surface called ELAMs (endothelial cell-leukocyte adhesion molecules). To date investigators have identified two of these molecules, intercellular adhesion molecule 1 (ICAM1) and endothelial cell-leukocyte adhesion molecule 1 (ELAM1). (Simmons et al., 1988; Staunton et al., 1988; and Bevilaqcua et al., 1987b.) ICAM1 is found on many cell types, and its expression on vascular endothelium is strongly upregulated both in vitro and in vivo by the inflammatory cytokines interleukin 1 (IL-1), tumor necrosis factor-α (TNF), and gamma interferon (IFN-γ). (Pober et al., 1986; Dustin and Springer, 1988; and Cotran and Pober, 1988.)

ELAM1 was initially detected and characterized by a monoclonal antibody (MoAb) that partially blocked PMN adhesion to cytokine-treated human umbilical vein endothelial cells (HUVECs). ELAM1 is a 116 kD cell surface glycoprotein rapidly synthesized by HUVECs in response to the inflammatory cytokines IL-1 or TNF, but not IFN-γ. (Bevilacqua et al., 1987b.) Unlike ICAM1, ELAM1 appears to be expressed only in endothelium, and its expression is transient even in the continued presence of cytokine. Like ICAM1, ELAM1 is present at inflammatory sites in vivo. Immunohistologic studies show that it exists at sites of acute, but not chronic, inflammation, and is absent from the non-inflamed vessel wall. (Cotran et al., 1986 and Cotran and Pober, 1988.) Therefore, ELAM1 appears to be a major mediator of PMN adhesion to the inflamed vascular wall in vivo. Importantly, the presence of ELAM1 on the cell surface follows the natural course of acute inflammation, appearing a few hours after stimulation and gradually dissipating within a day. (Bevilacqua et al., 1987b.)

Indirect evidence suggests that other ELAMs exist. Although inflammatory agents induce binding of PMNs, monocytes, and lymphocytes to endothelium in vitro, Moabs against ELAM1 inhibit only the binding of PMNs and related cells. (Bevilacqua and Gimbrone, 1987.) Furthermore, maximal accumulation of lymphocytes and monocytes at sites of inflammation in vivo occurs at about twenty-four hours, when ELAM1 expression has returned to basal levels. On the basis of such information investigators inferred the presence of other ELAMs that mediate binding of these lymphocytes and monocytes. (Bevilacqua et al., 1987b.) As set forth in detail below, we have characterized and cloned two more ELAMs, designated VCAM1 and VCAM1b, that mediate binding of lymphocytes to endothelial cells. ELAMs accordingly may be regarded as a family of molecules.

A growing body of evidence indicates that ELAMs may play important roles in a wide range of pathological states involving cell-cell recognition, including tumor invasion, metastasis and viral infection. (Harlan, 1985; Wallis and Harlan, 1986; Bevilacqua et al., 1987a; and Cotran and Pober, 1988.)

The adhesion of leukocytes to cells expressing ELAMs suggests the existence on leukocytes of ELAM ligands. One such molecule is the ICAM1 ligand, lymphocyte function associated antigen 1 (LFA1). LFA1 is one of a trio of heterodimeric molecules known as the $\beta 2$ integrins or the CD11/18 family. (Dustin et al., 1986; Rothlein et al., 1986; and Marlin and Springer, 1987.) Recent studies show that the ICAM1/LFA1 pathway plays a role in both lymphocyte and polymorphonuclear leukocyte (PMN) adhesion to endothelial cells in vitro. (Dustin and Springer, 1988; Smith et al., 1989.) We report here the isolation of a molecule involved in leukocyte adhesion to endothelial cells (MILA) which may prove to be an ELAM1 ligand. The molecule, designated CDX, is a 175 kD protein and was isolated from HL-60 cells. Monoclonal antibodies that recognize CDX inhibit the binding of PMNs and HL-60 cells to ELAM1-expressing cells. Furthermore, CDX is present on leukocyte cell types known to adhere to ELAM1 and is absent from leukocyte cell types and other cell types that do not adhere to ELAM1. Thus, CDX is a molecule expressed on certain leukocytes that plays an important role in ELAM1-mediated leukocyte-endothelial cell adhesion.

We also report the identification of a VCAM1 and VCAM1b ligand, VLA4. (Hemler and Takada, EP 330,506). Antibodies specific for the the $\alpha^4$ and $\beta_1$ subunits of VLA4 completely eliminate binding of VLA4-expressing cells to VCAM1.

Because leukocyte adhesion to the vascular all is the first step in inflammation, therapies directed to preventing this step are attractive for the treatment of pathologic inflammation. Clinicians are already testing, with some success, therapies based on inhibiting leukocyte-mediated adhesion. One such approach involves Moab binding to the leukocyte cell-surface complex, CD11/CD18, to inhibit PMN adhesion. (Arfors et al., 1987; Vedder et al., 1988; and Todd et al., 1989.)

We believe that alternative therapies for preventing leukocyte adhesion, based on endothelial cell-mediated binding, and on ELAMs and MILAs (including ELAM ligands), in particular, are more promising. The ELAM system is particularly appealing for two reasons: First, because ELAM expression on endothelial cells is induced rather than constitutive, ELAMs are concentrated at sites of inflammation and are limited in number. This means that adhesion inhibitors need act only locally and, consequently, would be effective at lower doses than inhibitors directed to constitutively expressed molecules. Second, ELAM binding is selective for different leukocyte classes. For example, ELAM1 binds PMNs, and VCAM1 binds lymphocytes. Therefore, these therapies would be specific for certain classes of leukocytes and would not affect the circulation or migration of other leukocyte classes. Furthermore, for the above reasons, such therapies may prove to be cheaper and less toxic.

ELAM-based approaches to therapy require, as starting materials, both ELAMs and MILAs in highly purified form, free of normally associated animal proteins. There is also a need for methods to produce these molecules. These and other needs have now been met as described herein, by isolating DNA sequences that code on expression for particular adhesion molecules and by constructing recombinant DNA molecules and expression vehicles for their production.

SUMMARY OF THE INVENTION

It is the principal object of this invention to provide new means to study, diagnose, prevent and treat inflammation. More particularly, it is an object of this invention to provide molecules involved in leukocyte binding to endothelial cells and to isolate other molecules which are themselves useful in inhibiting the endothelial cell binding of leukocytes.

This invention provides DNA sequences that code on expression for endothelial cell-leukocyte adhesion molecules (ELAMs), genomic DNA sequences for ELAMs (including ELAM expression control sequences), recombinant DNA molecules containing these DNA sequences, unicellular hosts transformed with these DNA molecules, processes for producing ELAMs, and ELAM proteins essentially free of normally associated animal proteins. The present invention also provides for antibody preparations reactive for ELAMs.

This invention also provides DNA sequences that code on expression for molecules involved in leukocyte adhesion to endothelial cells (MILAs). MILAs will include leukocyte surface molecules that bind directly to ELAMs, i.e., ELAM ligands. Monoclonal antibodies recognizing ELAM ligands can inhibit ELAM/ELAM ligand binding directly. MILAs will also include leukocyte surface molecules that are involved indirectly in adhesion, for example molecules that inhibit ELAM/ELAM ligand binding by interacting with a third molecule, such as a monoclonal antibody. Such molecules may act, for example, by changing the surface conformation of an ELAM ligand so that its affinity for the ELAM is reduced. This invention also provides recombinant DNA molecules containing MILA DNA sequences and unicellular hosts transformed with them. It also provides for MILA proteins essentially free of normally associated animal proteins and methods for producing MILAS. Also, it provides monoclonal antibodies that recognize MILAs, particularly CDX.

This invention further provides methods for inhibiting PMN binding to endothelial cells involving the use of ELAMs, MILAs including ELAM ligands, or portions of those molecules to block receptors or ligands. It also relates to the use of antisense nucleic acids and ribozymes to inhibit ELAM expression. The invention also relates to methods for identifying binding inhibitors by screening molecules for their ability to inhibit binding of an ELAM to its ligand. It provides methods for identifying ELAMs and their ligands. One such method involves using anti-idiotypic antibodies against antibodies that recognize ELAMs or ELAM ligands.

BRIEF DESCRIPTION OF THE DRAWINGS

FIG. 1 (A through E) depicts the composite ELAM1 cDNA sequence and deduced amino acid sequence derived from the DNA sequences of ELAM pCDM8 clone 6, pSQ148 and pSQ149. The nucleotides are numbered from 1 to 3863. Throughout this application we refer to the coding DNA sequence of this figure as the DNA sequence for ELAM1. We also refer to the molecule comprising the amino acid sequence depicted in this figure as ELAM1.

FIG. 2 depicts the DNA sequence of the synthetic polylinker of pNN11.

FIG. 3 (A through D) depicts the sequence of cDNA coding for VCAM1 and the deduced amino acid sequence of VCAM1 derived from AM pCDM8 clone 41. The nucleotides are numbered 1 to 2811. In this application we refer to the coding DNA sequence of this figure as the DNA sequence for VCAM1. We also refer to the molecule comprising the amino acid sequence depicted in this figure as VCAM1.

FIG. 4 (A through D) depicts the sequence of cDNA coding for VCAM1b and the deduced amino acid sequence of VCAM1b derived from VCAM1b pCDM8 clone 1E11. The nucleotides are numbered 1 to 3080. In this application we refer to the coding DNA sequence of this figure as the DNA sequence for VCAM1b. We also refer to the molecule comprising the amino acid sequence depicted in this figure as VCAM1b.

FIG. 5 depicts the domain structure of VCAM1. The amino acids are indicated according to the one letter code used by the University of Wisconsin Genetics Computer Group. (Devereux et al., 1984.)

FIG. 6 depicts the domain structure of VCAM1b. The amino acids are indicated according to the one letter code used by the University of Wisconsin Genetics Computer Group. (Devereux et al., 1984.)

FIG. 7 (A and B) depicts the DNA sequence of portions of the 5' untranslated and untranscribed region of ELAM1 derived from clone EL1-07.

DETAILED DESCRIPTION OF THE INVENTION

In accordance with this detailed description, the following definitions apply:

Expression control sequence—A DNA sequence that controls and regulates the transcription and translation of another DNA sequence.

Operatively linked—A DNA sequence is operatively linked to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

Antibody—An immunoglobulin molecule or functional fragment thereof, such as Fab, $F(ab')_2$ or dAb. An antibody preparation is reactive for a particular antigen when at least a portion of the individual immunoglobulin molecules in the preparation recognize (i.e., bind to) the antigen. An antibody preparation is non-reactive for an antigen when binding of the individual immunoglobulin molecules in the preparation to the antigen is not detectable by commonly used methods.

Standard hybridization conditions—salt and temperature conditions substantially equivalent to 5× SSC and 65° C. for both hybridization and wash.

DNA sequences—The DNA sequences of this invention refer to DNA sequences prepared or isolated using recombinant DNA techniques. These include cDNA sequences, DNA sequences isolated from their native genome, and synthetic DNA sequences. The term as used in the claims is not intended to include naturally occurring DNA sequences as they exist in Nature.

ELAM—A molecule expressed on the surface of endothelial cells that mediates adhesion of leukocytes to endothelial cells.

MILA—A molecule expressed on the surface of leukocytes that is involved in ELAM-mediated binding to endothelial cells. This includes ELAM ligands, i.e., molecules that bind directly to ELAMS.

As described below, we have isolated and sequenced cDNAs from ELAM mRNAs, expressed ELAM molecules in an appropriate host, identified and isolated MILAS, and isolated and expressed DNA sequences for MILAs.

Expression of recombinant DNA molecules according to this invention may involve post-translational modification of a resultant polypeptide by the host cell. For example, in mammalian cells expression might include, among other things, glycosylation, lipidation or phosphorylation of a polypeptide or cleavage of a signal sequence to produce a "mature" protein. Accordingly, as used herein, the terms ELAM and MILA encompass full-length polypeptides and modifications or derivatives thereof, such as glycosylated versions of such polypeptides, mature proteins, polypeptides retaining a signal peptide, truncated polypeptides having comparable biological activity, and the like.

ELAMs are expressed on the surface of endothelial cells only during inflammation. We utilized this phenomenon to isolate ELAM cDNAs. We have designated the polypeptides encoded by our cDNA isolates ELAM1, VCAM1 and VCAM1b. The first step involved in the isolation was selection of cells that differentially expressed the ELAM molecules. We chose human umbilical vein endothelial cells because they produce ELAMs when induced by the inflammatory cytokine, IL-1. However, the practitioner is not limited to this cytokine, to this cell type, or even to human cells in particular. Other mammalian cells, e.g., baboon endothelial cells, are also known to produce ELAMs. (Cotran and Pober, 1988.)

The next step was to isolate mRNA from cells expressing ELAMs, in this case, IL-1β-induced HUVECs, and to create a cDNA library from them. Many methods are known for isolating mRNA and for producing CDNA from it. (See, e.g., Gubler and Hoffman, 1983 and Maniatis et al., 1982.)

We then inserted the cDNA into an appropriate vector. We chose the eukaryotic expression vector pCDM8, described by Brian Seed. (Seed, 1987.) This plasmid has several advantages including a high copy number in E.coli, a eukaryotic promoter, and high level of expression in transient expression systems such as COS 7 cells. However, several other vector systems are available. (See, e.g., Cate et al., 1986.)

After constructing a cDNA library, the next step was to isolate from it clones containing ELAM cDNA sequences. There are currently many ways to isolate cDNA for a differentially expressed mRNA. These include, for example, (1) plus/minus screening with labeled cDNA; (2) production of subtracted cDNA libraries; and third, screening with subtractive cDNA probes. (Davis, 1986; Sargent, 1987; Davis et al., 1985, Hedrick et al., 1984; and Duguid et al., 1988.) We chose the third technique, screening with subtractive cDNA probes, and produced a cDNA sublibrary enriched for ELAM sequences.

As we will describe in more detail below, we produced a subtractive cDNA probe enriched for mRNA produced by cytokine-induced, but not uninduced cells. Then we probed the cytokine-induced cDNA library with the subtracted cDNA probe using techniques well known to the art. This enabled us to isolate clones forming a sublibrary enriched for ELAM sequences.

At this point we used two techniques to identify clones that contained cDNA for ELAM sequences. In a first method, we tested clones for expression of ELAM activity in an appropriate eukaryotic expression system. One can use a variety of direct expression techniques, including antibody screening of fusion proteins encoded by cDNA cloned in λAGT11 (Young and Davis, 1983; Young and Davis, 1984); or activity assay of oocyte-conditioned media after injection of mRNA from cloned cDNA, or from plasmid or phage DNA carrying SP6/T7 promoters. Alternatively, one can make libraries in plasmid, phage, and cosmid vectors containing a variety of promoter, selection and replication elements. Animal cells may be transfected with the library for transient or stable expression. Transfection can be accomplished by a variety of methods. For transient expression, investigators have used spheroplast fusion, DEAE dextran, and electroporation. For stable expression they have used calcium phosphate, spheroplast fusion, and electroporation. We used COS 7 cells, a transient expression system, transfected by spheroplast fusion. (Aruffo and Seed, 1987.)

Until recently, identification of cloned molecules by direct expression has required sensitive assays and has been restricted to lymphokines. However, cDNA cloning of single-chain cell-surface molecules in efficient transient expression vectors (see, e.g., Seed and Aruffo, 1987 and Seed, 1987), either by antibody "panning" technology (Wysocki and Sato, 1978) or by identification of functional molecules by FACS (Yamasaki et al., 1988), has expanded the range of cloned molecules that one can identify by direct expression. We have extended this technology by using an adhesion assay in that an appropriate cell type, expressing the ligand for the cloned molecule, is used to identify that molecule.

We detected ELAM expression by testing the ability of transfected cells to bind either the human neutrophil-like cell line, HL-60 (Bevilacqua et al., 1985), or the human B-lymphocyte-like cell line, RAMOS (American Type Culture Collection, ATCC accession no. CRL 1596, human Burkitt lymphoma). We describe this in more detail below. Because the transfected cells were nor-human, those producing human ELAM polypeptides did so in substantially purified form and essentially free of normally associated animal proteins. We picked cells that tested positive in this assay, collected the plasmid DNA, and isolated the inserts from them. These inserts contained DNA sequences encoding ELAM1 (selected by adhesion to HL-60 cells) and VCAM1 (selected by adhesion to RAMOS cells).

In a second method, we identified cDNA inserts from the enriched sublibrary that hybridized on a Northern blot to a 4 kb band of induced, but not uninduced, mRNA. Two of these inserts contained DNA sequences for ELAM1. Other inserts from the sublibrary encode different induced mRNAs.

We isolated a cDNA for another VCAM, VCAM1b, by probing the IL-1β-induced HUVEC cDNA library with a random-primed oligonucleotide $^{32}p$ probe derived from the VCAM1 cDNA sequence. VCAM1b is larger than VCAM1.

Using the clones identified by these three methods, we determined the sequences of cDNAs for ELAM1 and VCAM1 and 1b. It should be noted that due to the degeneracy of the genetic code, one may alter many of the nucleotides of these sequences and retain DNA sequences that code on expression for an amino acid sequence identical to those encoded by the DNA sequences we have presented in FIGS. 1, 3 and 4. Additionally, DNA sequences for fragments of the ELAM cDNA sequences, or DNA sequences that are substantially homologous to the ELAM cDNA sequences and that themselves encode ELAM polypeptides, would hybridize to the disclosed ELAM cDNA sequence under standard hybridization conditions.

From the DNA sequences described above, we deduced the amino acid sequences of ELAM1, VCAM1 and VCAM1b. It should be clear that given the current state of the protein-engineering art, an artisan could make purposeful alterations, insertions or deletions in these amino acid sequences and obtain a variety of molecules having substantially the same biological or immunological activities as those of the molecules we have disclosed herein.

We have also isolated genomic DNA sequences, including transcriptional promoters, for the ELAM1 and VCAM1 and 1b genes. We screened a human genomic library with $^{32}P$ labeled probes derived from the coding regions of the ELAM1 or VCAM1 DNA sequences. This yielded clones that contained portions of the 5' untranscribed and untranslated regions of both the ELAM1 and VCAM1 gene.

ELAM1 and VCAM1 transcriptional promoters have a number of uses. First, they are useful to construct vectors inducible by cytokines (such as TNF or IL-1), and bacterial lipopolysaccharide (LPS), or any other agent found to induce expression of ELAMs in endothelial cells. Such vectors may be useful, for example, in gene transfer assays, wherein the inducible promoter is positioned so that it drives transcription of a reporter gene such as chloramphenicol acetyltransferase, beta-galactosidase, luciferase, etc. This construct will then be introduced transiently or stably into an appropriate mammalian cell line. Potential inhibitors or stimulators of induction can then be assayed by measuring their effect on induction by any or all of the inducers listed above.

We have also isolated a hybridoma producing monoclonal antibodies recognizing ELAM1, designated BB11. We describe its production in Example V, infra.

VCAM1 is involved in T and B cell binding to endothelial cells. T cells activated by lectin stimulation or by a specific antigen bind to HUVECs in vitro. This binding is mediated in part by the ICAM/LFA1 pathway, since monoclonal antibodies that bind to an inhibitory epitope on CD18 (the common β chain of LFA1) partially inhibit T cell binding. We found that anti-CD18 and anti-VCAM1 monoclonals completely inhibit binding. Coupled with the observations that humans deficient in CD18 exhibit normal recruitment of lymphocytes to sites of inflammation, and that activated T cells do not recirculate through the lymphatic system (i.e., they will not exit from the blood stream except at sites of inflammation), this implies that VCAM1 is central to activated T cell migration in vivo. Thus, VCAM1 serves to focus all activated T cells into an inflammatory site. Since the presence of activated T cells is the hallmark of numerous inflammatory and autoimmune diseases, this in turn implies that inappropriate expression of VCAM1 might be the fundamental pathochemical characteristic of such diseases. Therefore, the VCAM1 pathway may provide a key intervention point for diseases where activated T cell recruitment is involved, e.g. arthritis, lupus, multiple sclerosis, etc. Therefore, we disclose a therapeutic treatment to inhibit T cell binding to the endothelium by blocking the VCAM1 binding pathway. This may be accomplished by any of the means we describe herein.

The DNA sequence of VCAM1 reveals that the molecule has no structural similarity to ELAM1 but is a member of the immunoglobulin supergene family. Three of the Ig superfamily members are established cell-cell adhesion molecules. These are NCAM, CEA, and ICAM1. NCAM binds to itself on the surface of other cells (homotypic adhesion) thus promoting adhesion between cells of the same type. The function of CEA was unknown until recently, when it was discovered to function as an adhesion molecule, mediating homotypic aggregation of colon tumor cells as well as cells transfected with the cDNA for CEA. (Benchimol et al., 1989.) ICAM1 is a ligand for the leukocyte surface protein, LFA1, and mediates both leukocyte-leukocyte and leukocyte-endothelial cell adhesion. (Staunton et al., 1988.) ICAM1 and VCAM1 possess some functional similarities, e.g., both are induced in endothelial cells after treatment with cytokines, and both mediate adhesion of lymphocytes and related cell lines. The ligand for ICAM1, LFA-1, has been well-characterized. The ligand for VCAM1 has been identified as VLA4 (see, infra). ICAM1 is believed to play a role not only in the migration of lymphocytes to sites of inflammation in vivo but also in numerous lymphocyte functions related to the immune response. Additionally, ICAM1 has recently been shown to be the receptor for many of the rhinoviruses. Receptors for other viruses (e.g., polio, HIV) are also members of the Ig superfamily. (White and Littmann, 1989.) Thus, VCAM1 may play a critical role in both immune regulation and viral infection.

Both CEA and ICAM1 are expressed on tumor cells. CEA has been used as a diagnostic marker for colon cancer for many years. Recent diagnostic techniques include the use of radioimmunoconjugates, in which anti-CEA antibodies are bound to radioactive markers and introduced into the patient. Using this method, clinicians have been able to identify tumors as small as three millimeters. (Goldenberg, 1989.)

Investigators are also exploring radioimmunotherapy and immunotoxin therapy. Radioimmunotherapy involves the use of radioimmunoconjugates in which nuclides such as $^{125}$I, $^{90}$Y, $^{186}$Re and the like are bound to antibodies recognizing a particular surface antigen. Immunotoxins are antibodies conjugated with cell toxins, such as Pseudomonas exotoxin and the like. Upon injection, these conjugated antibodies target the toxic agents to cells expressing the antigen. In accordance with this invention, radioactive markers, nuclides and cellular toxins may be conjugated with VCAM1 and 1b or antibodies recognizing them to target cells expressing VCAM1 ligands (e.g., VLA4) or VCAM1.

We have also found that incubating HUVECs with TNF and IFN-γ together increases VCAM1 expression about one-hundred percent over incubation with TNF alone. Activated T cells secrete IFN-γ, and therefore may promote their own recruitment to inflammatory sites through a positive feedback system: VCAM causes T cell binding, T cells further stimulate VCAM production via IFN-γ secretion. Thus, we have devised a new treatment for VCAM-dependent pathologies which involves inhibition of this feedback mechanism. The treatment comprises inhibiting cytokines such as IL-1, TNF or IFN-γ, for example with monoclonal antibodies, to block cytokine-stimulated production of VCAM.

We have also isolated a MILA, CDX, that is involved in ELAM1-mediated adhesion. The isolation involved, as a first step, the production of monoclonal antibodies against the CDX molecule. We immunized mice with whole HL-60 cells, a PMN-related cell line, that was known to bind to ELAM1. Alternatively, one could immunize with any cell line that binds to ELAM1, including PMNs themselves and, as we shall show, U937 cells. In addition, to isolate MILAs involved in adhesion to other ELAMs, one could immunize with any cell line that binds to the appropriate ELAM. For example, in isolating VCAM1, we have identified two such cell lines: The B-lymphocyte-like cell line, RAMOS, and the T-lymphocyte-like cell line, JURKAT.

After finding that immune serum from the immunized mice inhibited binding of HL-60 cells to HUVECs in the adhesion assay we will describe, we created hybridomas from spleen cells in a manner well known to the art. (Goding, 1983.) Then we identified those hybridomas that produced monoclonal antibodies (Moabs) against CDX by testing their ability in the adhesion assay to inhibit binding of HL-60 cells to induced HUVECs. We used several of these hybridomas to produce ascites fluid containing monoclonal antibodies.

One can also generate monoclonal Fab fragments recognizing these antigens using the technique of Huse et al. (1989). (See also Skerra and Plückthun, 1988.) Alternatively, one can produce single domain antibodies as described by Ward et al. (1989).

Our monoclonal antibodies against CDX possess the following characteristics: First, they inhibit binding of HL-60 cells or PMNs to cells that express ELAM1. Second, these antibodies exhibit a specific cell-binding pattern—they recognize cells that bind to ELAM1, but they do not recognize cells that do not bind to ELAM1. Third, they have a recognition pattern for human cell lines that is distinct from the pattern of antibodies against other cell-surface molecules, such as anti-LFA-1, anti-LFA-3, anti-p80, anti-ICAM, and anti-CD4.

We used these Moabs to isolate CDX. We radioactively labelled HL-60 surface proteins using a modification of a method described by Kurzinger. (Kurzinger et al., 1981.) We solubilized the membrane proteins and incubated them with an anti-CDX monoclonal (α-CDX Moabs), and then we isolated the antibody-bound proteins. The protein appears on SDS-PAGE as a single, diffuse band of about 175 kD. This protein is CDX isolated substantially free of normally associated animal proteins.

One can also isolate a DNA sequence that codes on expression for CDX using techniques known to the art. Some practical techniques involve using expression systems to express cloned DNA. As we have mentioned, a variety of eukaryotic expression systems are available. We have created a cDNA library from RNA of a cell line, HL-60, that expresses CDX. We are enriching this library for CDX DNA sequences by using subtraction techniques, as we have described, with a cell line that does not express CDX, such as HeLa cells. We have transfected a cell line, COS 7, with both the whole library and the subtracted library. We are identifying those cells expressing CDX in a number of ways. Functional clones may be identified by transient expression in, e.g., COS 7 cells, as described below.

First, we are incubating the transfected cells with the α-CDX Moabs and panning them on plates coated with anti-mouse IgG or IgM. Cells binding to the plates will be those expressing CDX. This method requires several rounds of isolating the plasmid DNA, retransfecting cells, and panning.

Second, we are taking advantage of fluorescent-antibody labelling. In this method, CDX-expressing cells are incubated with α-CDX Moabs and then the Moabs are labelled with fluorescently tagged anti-mouse antibody. Cells binding the fluorescent antibodies may then be sorted with a fluorescence activated cell sorter (FACS). The DNA from the sorted cells may be used to transform a bacterial host such as E. coli. DNA from the resulting colonies may be used to transfect COS 7 cells, and this procedure may be repeated until a single CDX-expressing clone is identified.

A third method is to pan the transfected cells as described above on plates coated with recombinant soluble ELAM1. We describe a method to coat plates with rsELAM1 in Example VIII. Cells binding to the plates will be those expressing CDX.

An expression library may also be created in E. coli. For example, a λ ZAP® (Stratagene)/HL-60 library may be constructed and used to express the inserted DNA in E. coli. After plating, the plaques can be directly screened with radioactively labelled α-CDX monoclonals. (Young and Davis, 1983 and Young and Davis, 1984.) The plaques to which the monoclonals bind can be picked and the DNA insert isolated from them.

Another method we are using to identify ELAM ligands, not based on antibody recognition, is to transfect COS 7 cells with an appropriate library, that may be subtracted, and then pan them directly onto ELAM-expressing cells (such as induced HUVECS, ELAM-expressing COS 7 cells, or ELAM-expressing CHO cells). Once again, multiple rounds of panning are required to enrich the library sufficiently to isolate the pertinent clones.

Another technique for isolating the DNA sequences coding for CDX involves screening a cDNA library with oligonucleotide probes. If sufficient CDX protein is purified, for example by affinity chromatography using immobilized antibody to CDX or immobilized ELAM1, one may determine a partial amino acid sequence and synthesize oligonucleotide probes that correspond to at least a portion of the CDX gene. These probes may then be used to screen the cDNA library.

We have also identified a ligand for VCAM1 and VCAM1b. It is the integrin VLA4. (Hemler, 1988; Hemler et al., 1987a; and Hemler et al., 1987b.) The integrins are a group of cell-extracellular matrix and cell-cell adhesion receptors exhibiting an α heterodimeric structure. (Hynes, 1987; Marcantonio and Hynes, 1988.) Investigators have identified three subfamilies of integrins categorized according to the β subunit. The VLA (Very Late Antigen) proteins belong to the $\beta_1$ subfamily, many of whose members are specialized for cell-extracellular matrix attachment. (Hynes, 1987 and Ruoslahti, 1988.) VLA4 is expressed in relatively high levels on lymphoid cells (such as B and T cells) and myeloid cells, but is hardly detectable in other cells (Hemler et al., supra.) The binding of B and T cells to the extracellular matrix is mediated by VLA4 and its ligand, human fibronectin (FN). (Wayner et al., 1989.) The discovery that VLA4 is a ligand for VCAM1 is important because it now defines one binding pathway of B and T lymphocytes to activated endothelial cells. Therefore, we describe the use of VLA4 and VCAM1 and 1b as ligand and receptor in the methods described below.

We contemplate several uses for ELAM and MILA DNA sequences and molecules in the present invention. First, one may use ELAMs and MILAs to produce monoclonal antibody preparations that are reactive for these molecules. The Moabs may be used in turn as therapeutic agents to inhibit leukocyte binding to endothelial cells.

Second, one may use a soluble form of ELAM, soluble ELAM ligand, or fragments of either as binding inhibitors. The ELAM peptides would bind to the ELAM ligand on leukocytes, and the ELAM ligand would bind to ELAM on endothelial cells. Both methods would thereby inhibit leukocyte binding to endothelial cells. To produce recombinant soluble ELAM (rsELAM) or rsELAM ligand one preferably would alter a DNA encoding those molecules to eliminate the transmembrane region. Thus, DNAs for soluble molecules would include all or part of the extracellular domain, perhaps attached to the cytoplasmic domain. This approach has already been validated using soluble CD4, the surface protein on T-cells that binds to the AIDS virus. (Fisher et al., 1988.) This approach also avoids the problems of antibody therapy, since the polypeptides used would be less likely to induce an immune response.

One problem investigators have encountered with soluble recombinant molecules is a short in vivo plasma half-life. (Capon et al., 1989.) Because such molecules are quickly cleared from the system, large doses or frequent injections are necessary to have a therapeutic effect. Therefore, investigators have sought methods to increase the half-life of soluble molecules. A potential solution is to link the soluble molecule to another molecule known to have a longer half-life in the blood stream. Due to their long half life, immunoglobulin molecules are promising candidates. Capon et al. (1989) have described the linking of soluble CD4 to an immunoglobulin molecule using recombinant DNA techniques. In this approach, one replaces the variable region of an immunoglobulin molecule with the soluble protein, forming a protein/immunoglobulin fusion protein.

Therefore, rsELAM/immunoglobulin fusion proteins will have greater plasma half-life than rsELAM alone. One produces these, preferably, with recombinant constructs, fusing a DNA sequence encoding the soluble molecule to a DNA sequence encoding the constant domain of an immunoglobulin molecule. Then one expresses this recombinant DNA in an appropriate host cell, preferably an animal cell.

We expect ELAM/immunoglobulin fusion proteins to have another advantage. Because immunoglobulin molecules are normally bivalent (i.e. they have two binding sites) an ELAM/immunoglobulin fusion protein would have two ELAMs and so, two ELAM ligand binding sites. Therefore, one would expect them to have greater affinity or avidity for cells displaying ELAM ligands.

Third, one may use molecules binding to ELAMs (such as anti-ELAM antibodies, or markers such as the ligand or fragments of it) to detect inflammation. This involves, for example, making a molecule detectable by fluorescence or radioactivity, administering it to a patient and determining where in the body it accumulates. In this way one could also identify the type of inflammation. For example, binding to ELAM1 would indicate acute, as opposed to chronic inflammation.

Fourth, if an ELAM binds to its ligand through a carbohydrate moiety or some other post-translational modification, one could use ELAM to identify the carbohydrate on the ELAM ligand to which it bound.

Fifth, one could use ELAMs and MILAs as part of a system to screen small molecules for adhesion inhibitors. For example, one could create an assay system in which small molecules are tested for the ability to inhibit the interaction between CDX and ELAM1.

Sixth, one could use these molecules to identify endogenous proteins that inhibit leukocyte binding to ELAMs. Investigators have tentatively identified one such molecule, leukocyte adhesion inhibitor (LAI), that is involved in detaching bound PMNs from endothelium. (Wheeler et al., 1988.)

Seventh, one can generate VCAM/ICAM fusion proteins. We know that both proteins are composed of several structural domains. (Simmons et al., 1988.) DNA sequences encoding various domains of each protein are fused using, for example, the genetic fusion techniques we describe for making ELAM/Immunoglobulin fusion proteins. The domains chosen are those having the ability to bind VCAM1 or VCAM1b ligands and ICAM1 ligands, respectively. Domains binding VLA4 and LFA1, the known ligands, are preferable. The polypeptides produced on expression of these DNA sequences are useful because they would block adhesion of any cell having a ligand to either VCAM1 or VCAM1b, or ICAM1 or both.

Finally, one could use ELAM and ELAM ligand DNA sequences to produce nucleic acid molecules that intervene in ELAM or ELAM ligand expression at the translational level. This approach utilizes antisense nucleic acid and ribozymes to block translation of a specific mRNA, either by masking that mRNA with an antisense nucleic acid or cleaving it with a ribozyme. These methods will be useful in treating inflammatory conditions.

Antisense nucleic acids are DNA or RNA molecules that are complementary to at least a portion of a specific mRNA molecule. (See Weintraub, 1990; Marcus-Sekura, 1988.) In the cell, they hybridize to that mRNA forming a double stranded molecule. The cell does not translate an MRNA in this double-stranded form. Therefore, antisense nucleic acids interfere with the expression of mRNA into protein. oligomers of about fifteen nucleotides and molecules that hybridize to the AUG initiation codon will be particularly efficient since they are easy to synthesize and are likely to pose fewer problems than larger molecules when introducing them into ELAM-producing cells. Antisense methods have been used to inhibit the expression of many genes in vitro. (Marcus-Sekura, 1988; Hambor et al., 1988.)

Ribozymes are RNA molecules possessing the ability to specifically cleave other single stranded RNA molecules in a manner somewhat analogous to DNA restriction endonucleases. They resulted from the discovery that certain mRNAs have the ability to excise their own introns. By modifying the nucleotide sequence of these RNAs, researchers have been able to engineer molecules that recognize specific nucleotide sequences in an RNA molecule and cleave it. (Cech, 1988.) Because they are sequence-specific, only mRNAs with particular sequences are inactivated.

Investigators have identified two types of ribozymes, Tetrahvmena-type and "hammerhead"-type. (Hasselhoff and Gerlach, 1988.) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore hammerhead-type ribozymes are preferable to Tetrahvmena-type ribozymes for inactivating a specific mRNA species, and eighteen-base recognition sequences are preferable to eleven-base sequences.

The DNA sequences described herein may thus be used to prepare antisense molecules against and ribozymes that cleave mRNAs for ELAM1, VCAM1 and VCAM1b, CDX and VLA4.

Antisense molecules and ribozymes may be used in methods to treat inflammation by introducing into cells molecules that interfere with the expression of adhesion molecules. Since ELAMs are induced on endothelial cells during inflammatory episodes, and since therapeutic agents can be delivered to vascular endothelium easily by intraveneous injection, endothelial cells are attractive targets for such therapies, provided the antisense molecules or ribozymes can be delivered effectively to the appropriate cells.

Investigators have suggested two approaches which could be used to deliver these molecules to target cells. The first involves transfecting the target cell with a vector that expresses the anti-ELAM antisense nucleic acid or the ELAM-specific ribozyme as an mRNA molecule. (Hambor et al., supra.) While this approach is very useful when dealing with cell lines in vitro, it may not be as effective in vivo. A second approach that is more promising for in vivo delivery involves loading liposomes with anti-ELAM antisense molecules, ELAM-specific ribozymes or vectors which express them. These liposomes could also contain anti-ELAM monoclonal antibodies to direct the liposome to sites of inflammation. This form of delivery would provide a negative feedback system, since appearance of an ELAM on a cell would make the cell a target for supression; and successful penetration of the antisense or ribozyme component would halt ELAM production, thereby eliminating the cell as a target.

Another feature of this invention is the expression of the ELAM and MILA DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAs, e.g., the numerous derivatives of phage λ, e.g., NM989, and other phage DNA, e.g., M13 and Filamenteous single stranded phage DNA; yeast plasmids such as the 2 μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences— sequences that control the expression of a DNA sequence operatively linked to it—may be used in these vectors to express the DNA sequences of this invention. Such useful expression control sequences, include, for example, the early and late promoters of SV40 or adenovirus, the lac system, the trp system, the TAC or TRC system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli*, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

The existence of antibodies against ELAM1, VCAM1 and 1b, CDX and VLA4 makes possible another method for isolating other ELAMs and ELAM ligands. The method takes advantage of an antibody characteristic known as idiotypy. Each antibody contains a unique region that is specific for an antigen. This region is called the idiotype. Antibodies, themselves, contain antigenic determinants; the idiotype of an antibody is an antigenic determinant unique to that molecule. By immunizing an organism with antibodies, one can raise "anti-antibodies" that recognize them, including antibodies that recognize the idiotype. Antibodies that recognize the idiotype of another antibody are called anti-idiotypic antibodies. Some anti-idiotypic antibodies mimic the shape of the original antigen that the antibody recognizes and are said to bear the "internal image" of the antigen. (Kennedy, 1986.) When the antigen is a ligand, certain anti-idiotypes can bind to that ligand's receptor. Investigators have identified several of these, including anti-idiotypes that bind to receptors for insulin, angiotensin II, adenosine I, -adrenalin, and rat brain nicotine and opiate receptors (Carlsson and Glad, 1989.)

Taking advantage of this phenomenon, other ELAMs and ELAM ligands may be isolated using anti-idiotypic antibodies. Anti-idiotypes may be used to screen for molecules binding to the original antigen. For example, one may use this technique to identify other ELAM ligands.

We have demonstrated that related ELAMs exist with similar domain structures (i.e. VCAM1 and VCAM1b.) As a result of gene shuffling, there may be several adhesion molecules on the cell surface that share one or more domains. Anti-idiotypic antibodies, which recognize any shared domains, are useful to isolate immunochemically ELAMs or ELAM-ligands not identified by bioassay, which relies on the protein's function, rather than structure.

In order that one may better understand this invention, we set forth the following examples. These examples are for purposes of illustration and are not to be construed as limiting the scope of the invention in any manner.

EXAMPLE I

PREPARATION OF A cDNA SUBLIBRARY ENRICHED FOR ELAM SEQUENCES

We prepared a CDNA sublibrary enriched for ELAM sequences as follows:

We isolated human umbilical vein endothelial cells (HUVECs) from umbilical cords, grew the cells in primary culture, and serially passaged them as described in Gimbrone (1976). We used HUVECs for library construction at passages 4 or 5. To induce the cells to produce mRNA for ELAMs we incubated confluent monolayers for 2.5 hours at 37° C. with recombinant human IL-1 (10 units/ml). We isolated the mRNA from these cells and reverse-transcribed it into cDNA using techniques well known to the art. (Gubler and Hoffman, 1983.) Using standard procedures, we ligated double stranded cDNA to a NotI-BstXI linker/adaptor having the following sequence:

5' GCG GCC GCT TTA GAG CAC A 3'
3' CGC CGG CGA AAT CTC 5'

We then size-selected the cDNA on a 4.2 ml 5–20% potassium acetate gradient, 2 mM EDTA, 1 µg/ml ethidium bromide, in a Beckman® SW60 Rotor for 3 hours at 50,000 rpm at 22° C. according to the protocols of Brian Seed. (See also Maniatis, 1982, p. 278.) We pooled the cDNA fragments of greater than 500 base pairs. Then we prepared the vector, pCDM8 (a gift from Brian Seed). We digested this plasmid with BstXI. To remove the 400 base pair stuffer fragment we centrifuged the mixture on a potassium acetate gradient, as above, and isolated the large fragment. We further purified this fragment by agarose gel electrophoresis, and then ligated the cDNA to the vector. In this way we created recombinant DNA molecules containing DNA sequences for mRNA expressed in induced HUVECS. We used these plasmids to transform *E. coli* MC1061 P3. The result was a collection of over 7×10$^6$ recombinant clones comprising a CDNA library for IL-1 -induced HUVEC mRNA.

In order to prepare from this cDNA library a sublibrary enriched for ELAM cDNA sequences, we first prepared a subtracted probe enriched for ELAM sequences. We prepared cDNA as above from HUVECs induced with IL-1 and labelled it with $^{32}$p. (Davis, 1986.) Then we isolated mRNA from HUVECs that had not been induced. To subtract uninduced cDNA sequences from induced sequences we hybridized the mRNA with the cDNA and isolated cDNA that had not hybridized to mRNA, as described by Davis (1986). We subjected the isolated cDNA to another round of subtraction to increase the level of enrichment. In all, we prepared three batches of subtracted probes enriched for ELAM sequences.

We tested the level of purification of the probe by Northern blot. (Lehrach et al., 1977.) We ran a gel with parallel lanes of polyA+ mRNA from induced and uninduced HUVECs and blotted it on Gene Screen® (New England Nuclear). Hybridization and subsequent autoradiography revealed that the probe bound strongly to a 4 kb band in the induced lane but did not bind, beyond background, to the uninduced lane. Occasionally we noted less intense hybridization bands to other messages in the induced lane.

We used the subtracted probe to create a cDNA sublibrary enriched for IL-1β induced sequences. We began by plating-out one million clones of the IL-1β-induced HUVEC cDNA library. We plated one million colonies on Gene Screen Plus® filters (New England Nuclear) on LB agar containing 12.5 μg/ml ampicillin and 7.5 μg/ml tetracycline, and grew them at 37° C. for 12 hours. We made two replicate filters (lifts) from each master. We grew these on LB agar containing 12.5 μg/ml ampicillin and 7.5 μg/ml tetracycline for 4 hours and amplified them on LB agar containing 250 μg/ml chloramphenicol for 16 hours. We lysed the filters according to manufacturer's protocol and then prehybridized them in Plaque Screen® Buffer (0.05 M TRIS-HCl pH7.5, 1 M NaCl, 1% SDS, 0.1% sodium pyrophosphate, 0.2% polyvinylpyrolidone (PVP), 0.2% Ficoll-400, 0.2% BSA). We hybridized the filters at 65° C. for 40 hours in 50 ml Plaque Screen® Buffer containing 10% dextran sulfate and 100 μg/ml yeast tRNA and approximately 1×10$^7$ cpm of the subtracted IL-1β-induced HUVEC cDNA. We then washed the filters twice with Plaque Screen® Buffer, twice with 2× SSC, 1% SDS, and twice with 1× SSC, 1% SDS at 65° C. We then exposed the filters to film for 5 days.

We selected colonies that hybridized to the probe by aligning the master filters with the autoradiographs and scraping the colonies off the filters with sterile toothpicks. We placed each scraping in one well of a 96-well microtiter plate filled with LB broth containing 7.5 μg/ml tetracycline and 12.5 μg/ml ampicillin. After innoculation, we incubated the microtiter plates overnight at 37° C. When the cells had grown we added glycerol to each well to a final concentration of 20% and stored the plates at −70° C. In this way we isolated from the master library filters 864 colonies comprising the cDNA sublibrary enriched for ELAM sequences. We point out that because of the plating density, not all the colonies of the enriched sublibrary were pure.

We carried out two sets of procedures in parallel with the enriched cDNA sublibrary.

EXAMPLE II

ISOLATION OF A CLONE EXPRESSING ELAM1

In a first procedure we isolated from the enriched sublibrary a clone expressing ELAM1. We chose to transfect this sublibrary into a cell line competent for high-level transient expression, the African Green Monkey kidney cell line, COS 7. We plated the cells and transfected the sublibrary by spheroplast fusion. (Sandri-Goldin et al., 1981.) Forty-eight hours after transfection, we assayed the COS 7 cells for expression of ELAM1 by their ability to bind HL-60 cells, a cell line known to bind to endothelial cells stimulated with inflammatory agents.

We performed the assay as follows: We labelled HL-60 cells with carboxyfluorescein diacetate according to the Brenan and Parish method. (Brenan and Parish, 1984.) Briefly, we resuspended HL-60 cells in RPMI/10% FCS at a concentration of 1×10$^7$ cells/ml, and added carboxyfluorescein diacetate to a final concentration of 0.1 mg/ml from a stock solution of 10 mg/ml in acetone. We incubated COS 7 cells with labelled HL-60 cells for 15 minutes at room temperature. We washed the cells 3–4 times with RPMI/1% FCS. We examined the petri dish by fluorescence microscopy for clusters of adherent HL-60 cells. We picked regions of the cell plates with clusters of HL-60 cells and lysed the cells in 0.6% SDS, 10 mM EDTA, pH 8, then rescued the plasmids according to the method of Hirt. (Hirt, 1967.) We used these pooled plasmids to transform *E. coli* MC1061 P3. We grew colonies from these transformants and performed a second round of spheroplast fusion with COS 7 cells with subsequent assay for HL-60 adhesion. From among the cells that were positive for adhesion we selected one and isolated the plasmid from it. We designated a culture containing this plasmid ELAM pCDM8 clone 6. We deposited this plasmid with In Vitro International, Linthicum, Md., U.S.A. on Apr. 20, 1989. It is identified as:

ELAM pCDM8 clone 6/*E. coli* MC1061 P3 Accession Number IVI-10204

EXAMPLE III

ISOLATION OF cDNA INSERTS FOR ELAM1 SEQUENCES

In a second procedure, we isolated cDNA inserts for IL-1β-induced cDNA sequences. We selected at random twenty-four of the 864 colonies of the enriched library and isolated plasmids from them using the alkaline miniprep procedure of Maniatis. (Maniatis, 1982.) We digested the plasmid DNA with XhoI or NotI and separated the fragments on 1% agarose gels. We identified from this gel two plasmids with inserts of greater than 3 kb, isolated these inserts and labelled them with $^{32}$P (Feinberg and Vogelstein, 1983 and 1984.)

Figure 2:
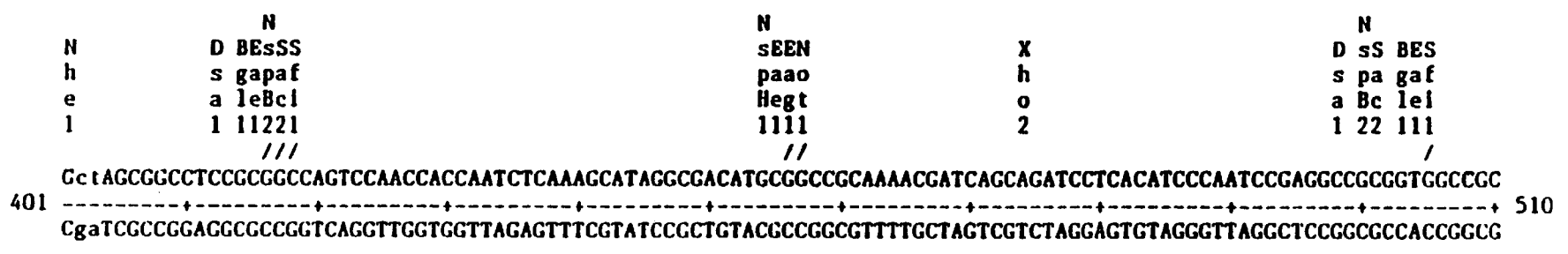

We then performed Northern blots with these inserts, as described above. Both inserts hybridized to bands at 4 kb in the induced HUVEC mRNA lane but did not hybridize to the uninduced HUVEC mRNA lane. The inserts cross-hybridized with the ELAM1 expressing plasmid ELAM pCDM8 clone 6 (described above) as well. We subcloned these inserts into NotI-digested pNN11 that had been treated with calf intestinal alkaline phosphatase. We constructed the sequencing plasmid pNN11 by removing the synthetic polylinker from the commercially available plasmid pUC8 (Pharmacia PL Biochemicals) by restriction digestion and replacing it with a new synthetic segment. The 2.5 kb backbone common to the pUC plasmids, that provides an origin of replication and confers ampicillin resistance, remained unchanged. The novel synthetic portion of pNN11 is shown in FIG. 2. We called these new constructs pSQ148 and pSQ149, respectively.

EXAMPLE IV

A DNA SEQUENCE FOR ELAM1

We determined the entire DNA sequence for the inserts of plasmids pSQ148 and pSQ149 and 624 nucleotides of the sequence at the 5' end of the insert of ELAM pCDM8 clone 6. We used the Maxam-Gilbert method. (Maxam and Gilbert, 1980.) Because the sequences have significant overlap, we obtained a composite sequence of ELAM cDNA, a sequence of 3863 nucleotides. This sequence consists of 140 nucleotides of the 5' untranslated region, 1830 nucleotides encoding 610 amino acids, and 1893 nucleotides of the 3' untranslated region (including a translational stop codon and a polyadenylation signal). The mature protein derived from the deduced amino acid sequence has been designated ELAM1, and the coding sequence has been designated the ELAM1 DNA sequence. The cDNA sequence of ELAM1 is shown in FIG. 1.

A search of the Genbank Data Base, release 58, December 1988, revealed that the DNA sequence for ELAM1 has no significant homologies to known DNA sequences.

We used this cDNA sequence to deduce the ELAM1 amino acid sequence, that is also presented in FIG. 1. Our analysis of the sequence revealed the following properties: The protein possesses a hydrophobic N-terminal sequence characteristic of a signal sequence. (von Heijne, 1986.) We have not yet determined the signal cleavage site and the mature N-terminus through protein sequencing, however based on von Heijne we predict that the mature N-terminal amino acid will be tryptophan, at nucleotide number 204 in FIG. 1. The extracellular domain of the polypeptide is approximately 554 amino acids including the signal sequence and is followed by a hydrophobic transmembrane region of 24 amino acids. The protein possesses a short, charged cytoplasmic tail of 32 amino acids. We note that the protein is cysteine-rich and contains eleven potential N-glycosylation sites.

When we compared the amino acid sequence of ELAM1 to other proteins in the NBRF and NEW protein data bases we found significant homology with several proteins, including complement C2 precursor, -2-glycoprotein I, C4b-binding protein, complement factor B, complement factor H, Drosophila notch protein, the IgE receptor Hepatic lectin, and Coagulation factors IX and X precursors. Thus, we can divide ELAM1 into at least three domains based on homology to the above-mentioned proteins: (1) a lectin-like domain (nucleotides 204–563 of FIG. 1); (2) an EGF-like domain (nucleotides 564–668); and (3) a consensus cysteine repeat unit of 59–63 amino acids containing six cysteine residues per repeat (nucleotides 669–1793). Other invariable amino acids in each repeat are proline, glycine, and tryptophan.

EXAMPLE V

MONOCLONAL ANTIBODIES RECOGNIZING ELAM1

To make monoclonal antibodies that recognize ELAM1 we prepared hybridomas in essentially the same manner as we did in Example X, infra. However, we immunized the mice with ELAM1-expressing COS cells and identified mice producing anti-ELAM1 antibodies by testing their antiserum for the ability to block HL-60 cell adhesion to IL-1β induced HUVECS.

We screened hybridomas produced in this manner for those producing anti-ELAM1 monoclonals using several assays. First, we tested the culture supernatants for antibodies having the ability to bind to a cell line that stably expressed ELAM1. This cell line was a line of CHO-DHFR⁻ cells transfected with the ELAM1 animal cell expression vector, pBG341jod.ELAM. We created this plasmid by introducing the DNA sequence encoding ELAM1 from pCDM8 clone 6 into the NtI site of pBG341.jod (described in Example VIII, infra). The ELAM1 expressing CHO-DHFR⁻ derived cell line was detected using an adhesion assay to HL-60 cells.

Second, we screened hybridoma culture supernatants for the ability to bind cytokine-induced, but not control, HUVECs.

Third, we tested them for their ability to inhibit HL-60 cell adhesion to cytokine-induced HUVEC monolayers.

We identified one hybridoma clone, BB11, which produced a positive result in all three assays. BB11 immunoprecipitates proteins with molecular weights of about 110 Kd and 96 Rd from ELAM1-expressing HUVECs and COS cells, representing variably glycosylated forms of ELAM1. (Bevilacqua et al., 1989) It also completely blocks adhesion of HL-60 cells to ELAM1-expressing COS and CHO cells. It produced immunoglobulins of the IgG$_{2b}$ class. We deposited a subclone of this hybridoma with In Vitro International on Dec. 13, 1989. It is identified as:

CDB.BB11.BC6 anti-ELAM1

Accession Number IVI 10220.

EXAMPLE VI

ISOLATION OF CLONES EXPRESSING VCAM1 and VCAM1b

We have also characterized and cloned two different ELAMs that bind to lymphocytes and lymphocyte-like cell lines. As a first step, we characterized the binding pathways of RAMOS, a B-lymphocyte-like line, and JURKAT, a T-lymphocyte-like line, to HUVECs induced with IL-1 or TNF for 4, 24, or 48 hours. We found that both RAMOS and JURKAT binding was maximal at 4 hours after induction with either IL-1 or TNF, and binding was maintained at 24 hours and 48 hours after induction. RAMOS binding was temperature-sensitive, occurring at room temperature but not at 4° C. JURKAT binding was reduced but not completely eliminated at 4° C., and thus JURKAT exhibited both a temperature-sensitive and temperature-insensitive component. Antisera from mice immunized with JURKAT cells inhibited binding from both JURKAT and RAMOS cells to HUVECs, indicating that RAMOS and JURKAT share a MILA. Neither RAMOS nor JURKAT bound to COS or CHO cells expressing ELAM1, indicating the presence of at least one other inducible ELAM on HUVECs, at 4 to 48 hours after induction.

In order to isolate clones expressing the ELAMs involved in RAMOS and JURKAT binding to HUVECs, we screened the previously described ELAM-enriched HUVEC cDNA sublibrary by the method described in Example II, supra. We incubated carboxy-fluorescein diacetate-labelled RAMOS and JURKAT cells with sublibrary-transfected COS 7 cells. Regions of the cell plates with clusters of bound cells were picked and lysed, and the plasmids were rescued, transformed into E. coli, and reassayed in COS 7 cells as previously described. Plasmids were isolated from individual bacteria colonies from the transformants that were positive on reassay. These plasmids were transfected individually into COS 7 cells, and a plasmid that tested positive for adhesion to RAMOS and JURKAT was identified. The cDNA insert from this plasmid was excised, radioactively labelled, and used to probe a Northern blot according to the procedures of Lehrach (1979). The probe hybridized to an RNA species approximately 3.4 kb in length. The RNA was undetectable in uninduced HUVEC RNA, barely detectable at 5, 10, 30 or 60 minutes after treatment with IL-1, but abundant at 2, 24, 48 and 72 hours after treatment with IL-1.

We designated the plasmid AM pCDM8 clone 41. We deposited this plasmid with In Vitro International on May 24, 1989. It is identified as:

AM pCDM 8 clone 41/ E. coli MC1061 P3

Accession Number IVI-10206

We have also isolated a cDNA for another VCAM. We screened the IL-1β-induced HUVEC cDNA library (Example I) with a labelled VCAM1-encoding insert from AM PCDM 8 clone 41. We sequenced one of these, clone 1E11. We found several clones that were longer than the clone 41 insert as analyzed by restriction mapping with XbaI. We sequenced one of these, clone 1E11. We deposited it with In Vitro International on Dec. 7, 1989. It is identified as:

VCAM 1B clone 1E11 pCDM8/E. coli MC1061p3

Accession Number IVI-10216.

We are also isolating DNA sequences for other ELAMs. We are collecting mRNA from HUVECs around forty-eight hours after IL-1 induction. We will isolate the ELAM cDNA sequences in a manner similar to the one we used to isolate the cDNA sequences for ELAM1 and VCAM1 and 1b.

Alternatively, one may identify other ELAMs by inducing cells with other inflammatory agents, such as TNF, LT, LPS, interferons, or combinations of such agents.

EXAMPLE VII

DNA SEQUENCES FOR VCAM1 and VCAM1b

We determined the entire DNA sequence for the insert of plasmid AM pCDM8 clone 41 by the method of Maxam and Gilbert (1980). This sequence consists of 106 nucleotides of the 5' untranslated region, 1941 nucleotides encoding 647 amino acids, and 764 nucleotides of the 3' untranslated region including a translational stop condon. The protein derived from the CDNA sequence has been designated VCAM1, and the coding sequence has been designated the VCAM1 DNA sequence. We have presented the cDNA sequence of VCAM1 in FIG. 3. The putative amino acid sequence of VCAM1 is also indicated in FIG. 3.

We also determined the entire DNA sequence for the insert of plasmid VCAM1b pCDM8 1E11 by the method of Maxam and Gilbert (1980). This sequence consists of 99 nucleotides of the 5' untranslated region, 2217 nucleotides encoding 739 amino acids and 764 nucleotides of the 3' untranslated region including a translational stop codon. We have designated the mature protein derived from the cDNA sequence as VCAM1b and the coding sequence as VCAM1b DNA sequence. We have presented the cDNA sequence and putative amino acid sequence of VCAM1b in FIG. 4.

Comparison of the DNA and amino acid sequences of VCAM1 and VCAM1b revealed that they are virtually identical except for one significant difference: VCAM1b contains an insertion of 276 nucleotides near the middle of the coding region. These nucliotides encode 92 additional amino acids including an extra domain of 84 amino acids and changes at the end of VCAM1 domain 3 and beginning of VCAM1 domain 4. We discuss the significance of this domain below.

Our analysis of the sequences revealed the following properties: The VCAM1 polypeptide possesses a hydrophobic N-terminal sequence characteristic of a signal sequence. (von Heijne, 1986.) We have not yet determined the signal cleavage site and the mature N-terminus through protein sequencing, however based on von Heijne we predict that the N-terminal amino acid of the mature protein will be phenylalanine, at nucleotide number 179 in FIG. 3. The extracellular domain of the polypeptide is approximately 606 amino acids including the signal sequence and is followed by a hydrophobic transmembrane region of 22 amino acids. The protein possesses a short, charged cytoplasmic tail of 19 amino acids. We note that the protein contains six potential N-glycosylation sites.

Similarly, the N-terminal amino acid of the mature VCAM1b protein should be the phenylalanine, at nucleotide number 172 of FIG. 4. The extracellular domain of the polypeptide, which is longer than VCAM1, is approximately 698 amino acids including the signal sequence and is followed by a hydrophobic transmembrane region of 22 amino acids. The protein possesses a short, charged cytoplasmic tail of 19 amino acids. We note that the protein contains seven potential N-glycosylation sites.

Comparison of the amino acid sequences of VCAM1 and VCAM1b with other proteins in the NBRF and NEW protein databases revealed significant homologies with several proteins, including non-specific cross-reactive antigen (NCA), biliary glycoprotein 1 (BG1), neural cell adhesion molecule (NCAM), carcinoembryonic antigen (CEA), immunoglobulin alpha chain constant region, the T cell receptor (TCR) alpha and beta chain variable regions, and myelin associated glycoprotein (MAG). Lesser homology is seen with myosin light chain kinase, ribulose biphosphate carboxylase, adenovirus E1A 28K protein, pseudouridine synthetase, and xylulokinase. VCAM1 and 1b and the VCAM1 and 1b DNA sequences show no homology with, and are distinct from, the previously described ELAM1 (supra).

Importantly, NCA, BG1, NCAM, CEA, MAG, and TCR are members of the immunoglobulin gene superfamily. (Williams and Barclay, 1988; Hunkapiller and Hood, 1989.) Members of this family are defined by the presence of one or more regions homologous to the basic structural unit of immunoglobulin (Ig) molecules, the Ig homology unit. (Hunkapiller and Hood, 1989). These units are characterized by a primary amino acid sequence of about 70–110 residues in length, with an essentially invariant disulfide bridge spanning 50–70 residues, and several other relatively conserved residues involved in establishing a tertiary structure referred to as the "antibody fold". These units may be further subdivided into three groups, i.e., V, C1, and C2 (Williams and Barclay, 1988), or V, C, and H (Hunkapiller and Hood, 1989), based on various criteria, including intercysteine spacing, number of beta strands, and type of conserved residues. When these criteria are applied to the predicted primary sequence of VCAM1, the sequence can be divided into six Ig units, designated domains 1–6, all of which fall into the C2 or H subset, each of about 100 amino acids in length. The invariant disulfide bridges of the six domains, referring to FIG. 3, occur between cysteines 47 and 95 (Domain 1), 137 and 195 (Domain 2), 246 and 291 (Domain 3), 333 and 391 (Domain 4), 442 and 487 (Domain 5), and 531 and 576 (Domain 6).

As we stated above, VCAM1b has seven domains. We have designated the additional domain as Domain 3B. This domain is included in the additional 276 nucleotides of VCAM1b that begin at nucleotide 1027 and end at nucleotide 1305 of FIG. 4. The DNA sequence encompassing Domains 1–3 is 72% homologous to the DNA sequence encompassing Domains 3B-5. At the polypeptide level, there is significant homology between domains 1 and 3B, 2 and 4, and 3 and 5, respectively. We present the domain structures of VCAM1 and VCAM1b in FIGS. 5 and 6.

EXAMPLE VIII

RECOMBINANT SOLUBLE ELAM1 AND VCAM1

We constructed a vector expressing recombinant soluble ELAM1 (rsELAM1). We called this hector pSAB108. The rsELAM1 expressed by pSAB108 contains the portion of the extracellular domain of ELAM1 encoded by the DNA sequence of FIG. 1 from nucleotide 141 to nucleotide 1790.

To construct pSAB108 we first created a DNA fragment which encoded an rsELAM1. We digested ELAM pCDM8 clone 6 with MluI and NotI. This yielded a 3.8 kb DNA fragment including a DNA sequence encoding ELAM1. We subcloned this fragment into NotI-digested pNN11 that had been treated with calf intestinal alkaline phosphatase (described in Example III). We called this vector PNNELAM1.

We used site specific mutagenesis to eliminate the transmembrane and intracellular regions of ELAM1. (Peden and Nathans, 1982; Kalderon et al., 1982; Oostra et al., 1983.) Accordingly, we digested a sample of pNNELAM1 with EcoRI and isolated the large fragment. We linearized another sample of pNNELAM1 with ScaI. Then we synthesized an oligonucleotide having the sequence 5' TGT GAA GCT CCC TAA ATT CCC. When this sequence hybridizes to an ELAM1 antisense sequence it introduces a stop codon and a BamHI restriction site into the ELAM1 DNA sequence after nucleotide number 1790. We created a heteroduplex using these three fragments according to the methods of Morinaga et al. (1984) and Chang et al. (1984). We filled in the single stranded gaps with Klenow fragment and T4 ligase and used the mixture to transform *E. coli* MC1061. We screened the resulting colonies by checking for a BamHI site and selected mutagenized clones. Consequently on expression, the transmembrane region of the polypeptide is eliminated and the C-terminal amino acid is proline. We called this plasmid pSAB100.

Then we digested pSAB100 with AatII and NcoI and isolated the 5.2 kb fragment. We also digested pNNELAM1 with these two enzymes and isolated the 1.4 kb fragment. NcoI cuts at nucleotide 927 of FIG. 1, about the middle of the ELAM1 coding area. We ligated these two DNA fragments and called the plasmid pSAB108. We made this construction because site-directed mutagenesis sometimes causes mutations in other parts of the molecule and we wanted to avoid any such mutations in the coding region of rsELAM1. We digested pSAB108 with NotI and isolated the 3.8 kb fragment. We ligated this fragment to a 7819 bp fragment of pBG341.jod, created as follows.

First we obtained pSV2-DHFR, ATCC 37146, from the American Type Culture Collection, Bethesda, Md., U.S.A. (Subramani et al., 1981.) We digested this with ApaI and EcoRI and isolated the 4420 bp fragment. Then, we produced a synthetic double stranded DNA sequence having an ApI overhang, a DNA sequence encoding nucleotides +190 to +233 of the human gastrin gene (Sato et al., 1986, FIG. 4), an XhoI site, and an EcoRI overhang. We ligated this oligonucleotide with the 4420 bp fragment of pSV2-DHFR and called the resulting plasmid pDT4. We digested this plasmid with AatII and XhoI and isolated the 4391 bp fragment.

Then we cleaved the Mullerian inhibiting substance expression vector pD1 (Cate et al., 1986) with AatII and SalI and isolated the 5462 bp fragment. We ligated fragment with the 4391 bp fragment of pDT4 to make pJOD-10.

We digested pJOD-10 with HindIII and BstEII and isolated the large fragment which did not encode Mullerian Inhibiting Substance. We blunt-ended the fragment ends, ligated SalI linkers to the ends and self-ligated the vector. This produced pJOD-s.

Then we digested pJOD-s with AatI and NotI and isolated the 6750 bp fragment. We ligated this to a 1100 bp NotI fragment from pBG341, which we created as follows.

We created pBG341 by replacing the SmaI site of pBG312 (Cate et al., 1986) with a NotI site. We linearized pBG312 with BglII, blunt-ended the fragment by filling in with Klenow, and self-ligated it. We linearized this plasmid with BamHI and again blunt-ended and self-ligated it. We linearized this plasmid with SmaI and ligated to the ends a NotI linker having the sequence 5' GCGGCGC. We called the resulting plasmid pBG341.

We digested pBG341 with AatII and NotI and isolated the 1100 bp fragment. We ligated this fragment to a 6750 bp fragment of pJOD-s. We called the resulting plasmid pBG341.jod. This plasmid contains the SV40 early and the adenovirus major late promoter. Genes inserted into the plasmid at the NotI site are transcribed from either of these promoters.

Then we linearized pBG341.jod with NotI and isolated the linear 7819 bp fragment. We ligated this fragment with the 3.8 kb fragment of pSAB108, which encoded rsELAM1, generating plasmid pSAB110.

We transfected CHO-DHFR- cells by electroporation with plasmid pSAB110 linearized with AatII. electroporation. We performed electroporation with a Biorad Gene Pulser® at 270V and 960 μFD using $10^7$ cells/ml in 20 mM Hepes pH 7.05, 137 mM Nacl, 5 mM KCl, 0.7 mM $Na_2HPO_4$, and 6 mM dextrose with 20 μg plasmid and 200 μg sonicated salmon sperm DNA. Following transfection we cultured the cells in selective medium, alpha minus MEM containing 500 nM methotrexate and 10% dialyzed FCS. We picked colonies, plated them onto 96-well cluster plates and detected rsELAM1-expressing cells using the monoclonal antibody BB11. After growing cells to confluence in complete medium containing 10% fetal calf serum (FCS) we maintained them in medium containing 2% FCS in which the cells produced rsELAM1. We harvested medium and replaced it with fresh 2% serum every three or four days.

We isolated rsELAM1 from this conditioned medium to at least 95% purity. This involved concentrating the medium and incubating it overnight with Moab BB11 (Example V) covalently coupled to Protein A Sepharose®. (Schneider et al., 1982) Then we washed this resin with PBS to remove unbound protein, eluted bound material with 0.1 M glycine, pH 2.7, neutralized the eluate with sodium phosphate and dialyzed it against PBS. We further purified the rsELAM1 by chromatography with protein A Sepharose in PBS.

Using the following assay, we demonstrated that we had produced rsELAM1. To a 6 cm diameter Petri dish of bacteriologic plastic (e.g. Falcon #1007®) we added 2.5 ml of 50 mM Tris buffer, pH 9.5. To this we added 10 μg of pure rsELAM1. We incubated the plate for 60 minutes at room temperature to allow the rsELAM1 to bind to the plate. Then we aspirated the medium and replaced it with PBS containing 10 mg/ml bovine serum albumin. We incubated the plates overnight at 4° in this solution to block remaining protein binding sites on the plates. We warmed the plates to room temperature, washed them with medium containing 10% fetal calf serum, and incubated them with 2 ml of cells ($2\times10^6$ $ml^{-1}$) for 20 minutes. We aspirated the medium and washed the plates twice with 3 ml each of medium (RPMI1640 with 10% serum). Then we examined the plates by microscopy.

We found that cells which bind ELAM1, such as HL-60 cells, bind to rsELAM1-coated plates, while cells which do not bind to ELAM1 e.g. the B cell line RAMOS, do not bind to these plates.

In addition, we found that the specific Moab BB11 blocks the binding of HL-60 cells to rsELAM1 coated plates. Together, these results show first, that we have produced rsELAM1, and, second, that like ELAM1, rsELAM1 possesses the ability to bind to leukocytes.

EXAMPLE IX

ISOLATION OF THE ELAM1 AND VCAM1 PROMOTER

We have isolated and characterized genomic clones for the ELAM1 and VCAM1 genes. We isolated the ELAM1 clones as follows:

We selected as probes either the entire ELAM PCDM8 clone 6 insert or a 400 base pair fragment from its 5' end. We labeled these molecules with $^{32}p$ by random priming. Then we screened a human genomic EMBL3 library with the ELAM cDNA probes. We isolated and characterized a genomic ELAM1 clone from the library and designated it EL1-07. It includes approximately 15 kb of 5' flanking sequence including the transcriptional promoter for ELAM1 and approximately 100 base pairs of coding sequence at the 5' end of the gene. Current knowledge suggests that the relevant control sequences for induction will be included within the DNA sequence represented by this phage clone (Leonardo and Baltimore, 1989). We sequenced a region including 840 bp of 5' flanking sequence and 720 bp of the 5' end of the ELAM1 gene, including the first two exons, the first intron and part of the second intron. We present this sequence in FIG. 7. The 5' flanking region displays a classical promoter structure including TATAAA and CAAT sequences. It also contains the sequence GGGGATTTCC about 95 base pairs upstream from the presumed start of transcription. This sequence is an NF-κB binding sequence identical to that found in the human κ immunoglobulin (Ig) gene enhancer. NF-κB is an inducible DNA binding protein known or suspected to stimulate transcription of a number of genes relevant to inflammation and the immune response (such as the immunoglobulins, the interleukin-2 receptor, and β-interferon, among others). It can be activated by TNF, IL-1, and LPS, the same inducers known to stimulate production of ELAM1, VCAM1, and ICAM1. (Lenardo and Baltimore, 1989; Osborn et al., 1989.) We have demonstrated that NF-κB DNA binding activity is stimulated in endothelial cells by IL-1 and TNF, and we are currently engaged in defining minimal DNA sequences necessary for inducible transcription from the ELAM1 promoter, by transfection of promoter/reporter gene constructs into endothelial and other cell types.

We deposited clone EL1-07 with In Vitro International on Dec. 7, 1989. It is identified as:

EL1-07

Accession Number IVI-10218.

We also isolated an EMBL3 genomic clone representing the VCAM1 gene by probing the previously mentioned EMBL3 human genomic library with a $^{32}p$-labelled 30 base oligomer probe homologous to the 5' end of the VCAM1 cDNA. We designated this clone VC1-16 and deposited it with In Vitro International on Dec. 7, 1989. It is identified as:

VC1-16

Accession Number IVI-10217.

We localized the VCAM1 promoter sequence to a HindIII fragment of approximately 1 kb and are currently cloning this fragment in preparation for sequencing and functional analysis as described above for ELAM1.

EXAMPLE X

ANTIBODIES RECOGNIZING CDX

We isolated CDX, a MILA involved in ELAM1-mediated adhesion. As a first step, we prepared monoclonal antibodies that recognized an antigen on the leukocyte cell surface and that interfered with leukocyte-endothelial cell binding. In order to assure that the antigen that these monoclonals recognized was involved in ELAM1-mediated adhesion, we tested the monoclonals in systems in that ELAM1-mediated binding was the exclusive cell-cell binding pathway.

1. Preparation and Analysis of Monclonal Antibodies Against CDX a. Adhesion assay To identify Moabs that inhibit leukocyte-endothelial cell binding, we developed an improved assay to detect endothelial cell-leukocyte adhesion. We performed this assay using HL-60 cells and HUVECS. It should be clear that one can perform such an assay using any cell line that expresses a MILA and with any cell line that expresses an ELAM. In 48-well tissue-culture plates we grew HUVECs to confluence. ($8 \times 10^4$ cells/well). We washed the cells once with RPMI/1% FCS and added 0.5 ml RPMI/1% FCS with 13 U/ml of IL-1 to each well (except the control wells). We incubated these cells for 4 hours at 37° C. Just before use, we washed them once with RPMI/1% FCS. The HL-60 cells we used in the assay had been labeled overnight with 1 $\mu$Ci/ml of $^{35}$S-methionine. We washed these cells once and then resuspended them in RPMI/1% FCS at $5 \times 10^6$ cells/ml. We took 100 $\mu$l of the HL-60 cells and incubated them for 30 min. at 0° C. with 50 $\mu$l of Moab (1 Mg/ml). Then we added the 150 $\mu$l to each well of HUVECs. We allowed the cells to bind for 10 min. at 20° C. and then washed the wells gently once with RPMI/1% FCS. We filled the wells with RPMI/1% FCS, sealed the plates, inverted them, and centrifuged them for 2 min. at 500× g. We removed the media and washed the wells two more times with PBS⁻. (PBS⁻ is PBS without $Ca^{++}$ and without $Mg^{++}$.) We determined the number of HL-60 cells bound to the HUVECs by solubilizing the cells in each well with 200 $\mu$l of 0.2 N NaOH/1% SDS, adding 4.5 ml of scintillant (Ready Protein, Beckman), and counting with a scintillation counter.

b. Preparation of hybridomas

To make monoclonal antibodies against CDX we prepared hybridomas in the following manner. We injected BALB C mice with whole, live HL-60 cells. Initially, each mouse received $2 \times 10^7$ cells in PBS⁻ intraperitoneally (IP). We injected complete Freund's adjuvant intraperitoneally at a different site 2–24 hours later. We boosted the mice with $2 \times 10^7$ cells IP every second week for six weeks. Four days before fusing we injected the mice intravenously with $5 \times 10^6$ cells and IP with $5 \times 10^6$ cells.

We tested immune serum from these animals for the ability to inhibit binding of the HL-60 cells to IL-1 stimulated HUVECs by the adhesion assay described above. The immune serum tested positive after the third boost and we proceeded to produce hybridomas from the spleen cells of the immunized animals. We performed fusion of spleen cells and myeloma cells in a manner standard to the art. (See, Goding, 1983.)

Using the adhesion assay we described above, we screened the hybridomas for those producing monoclonal antibodies that inhibited the binding of HL-60 cells to IL-1-induced HUVECS. In this way we identified hybridomas that produced monoclonal antibodies that recognized CDX. We used five of these hybridomas to produce ascites fluid. We deposited one of them, designated $SGB_3B_4$, with In Vitro International, Linthicum, Md., U.S.A. on Apr. 25, 1989. It is identified as:

$SGB_3B_4$

Accession number: IVI-10205 c. FACS analysis

To identify to which cell types our monoclonals bound, we performed FACS analysis. This involved taking $2 \times 10^5$ cells, washing them one time with PBS$^-$, and then blocking Fc receptors by incubation in 25 µl of RPMI, 1% FCS, 0.1 mg/ml human IgG, and 0.1% sodium azide for 10 min. at 0° C. We then added antibody (25 µl at 1 µg/ml) and incubated the cells 30 min at 0° C. We centrifuged the cells at 250× g for 5 min., washed them two times with Buffer A (PBS$^-$, 5% FCS, 0.1% azide) and resuspended them in 25 µl Buffer A containing 0.1 mg/ml human IgG. We added fluorescine-conjugated anti-mouse IgG (25 µl at 5 µg/ml in Buffer A (Cappel)) and incubated the mixture 30 min at 0° C. We centrifuged the cells, washed them once with Buffer A, and resuspended them in 250 µl Buffer A. Then we analyzed them on a Beckton-Dickinson FACStar Cell Sorter.

We performed cell binding studies with the ELAM1-expressing COS cells essentially as described for the HL-60 cell-HUVEC adhesion assay.

2. Demonstration That Hybridoma $SGB_3B_4$ Produced Monoclonal Antibodies Teat Recognize CDX We have developed several lines of evidence that demonstrate the specific recognition of monoclonals from hybridoma $SGB_3B_4$ for a MILA involved in ELAM1-mediated binding, specifically, CDX.

First, the α-CDX antibodies should inhibit binding of cells expressing CDX to ELAM1-expressing cells. Using the adhesion assay, we showed that these monoclonals do indeed inhibit the binding of HL-60 cells and PMNs to IL-I -induced HUVECs and ELAM1-expressing COS 7 cells. The only binding pathway for HL-60 cells and PMNs that is utilized in ELAM1-expressing COS 7 cells is ELAM1 itself. Therefore, antibody inhibition of cell-cell adhesion in this system must be through the ELAM1 pathway via CDX.

Second, α-CDX monoclonals should recognize those cells that bind to ELAM1-expressing cells in an adhesion assay, but should not recognize those cells that do not bind to ELAM1 in this assay. Using FACS analysis, we determined the binding pattern of our Moabs. These monoclonals bound to the following cell types: HL-60, U937, HT-29 and PMNs. They did not bind to these cells: RAJI, DAUDI, RAMOS, HeLa, T-cells, or B-cells. (We isolated the non-transformed cells by fractionating peripheral blood leukocytes.) This binding pattern precisely parallels the binding of these cells to ELAM1-expressing COS 7 cells.

Third, α-CDX monoclonals should exhibit a different recognition pattern than monoclonals against other leukocyte cell-surface antigens, such as LFA-1, LFA-3, p80, ICAM1 and CD4. In fact, no other monoclonal of that we are aware exhibits the same cell-recognition pattern as our antibodies.

In sum, it is apparent that the monoclonals produced by hybridoma $SGB_3B_4$, and by other hybridomas we isolated, recognize CDX. Consequently, we used these monoclonals to isolate CDX itself.

EXAMPLE XI

ISOLATION OF CDX

1. Iodination of HL-60 Cell Surface Proteins

We washed $2 \times 10^7$ HL-60 cells three times with PBS$^-$, resuspended them in 0.5 ml. PBS$^-$ and added them to a tube coated with 100 µg 1,3,4,6-tetrachloro-3α,6α-diphenylglycouril (Sigma Chemical Co.). To this we added 1 mCi of $^{125}$I. We incubated the mixture for 30 min at 0° C. We quenched the reaction with cold tyrosine and then cold NaI. We transferred labelled cells to a tube containing 10 ml of RPMI/10% FCS and centrifuged them at 1000× g for 5 min. Then we washed them first with another 10 ml of RPMI/10% FCS and second with 2 ml of PBS$^-$. We lysed the cells by addition of 1.0 ml PBS$^-$ containing 1% NP40, 2 mM PMSF, 1 mM EDTA, soybean Trypsin inhibitor (50 mg/ml), and Leupeptin (1 mM) (Sigma Chemical Co.). Then we incubated them for 30 min at 0° C. We centrifuged the lysate for 10 min. at 10,000× g to remove particulate matter. We precleared the supernatant containing labelled solubilized membrane proteins with 10 µg of rabbit anti-mouse IgM (Jackson Immuno-Research Labs) and 50 µl of protein G sepharose (Zymed, 2 mg protein G/ml) for 1 hour at 0° C. We stored the lysate at 4° C.

2. Immunoprecipitation of CDX

We purified CDX away from the other labelled proteins using the Moabs to immunoprecipitate it. We performed the immunoprecipitation as follows:

We incubated precleared lysate (50–100 µl) with 5 µg of α-CDX monoclonals for 2 hours at 4° C., then added 10 µg of Rabbit-anti-mouse IgM and incubated the lysate for another hour at 4° C. To precipitate molecules bound to these antibodies, we added Protein G Sepharose (10 µl) and rocked the mixture for 16 hours at 4° C. We washed the Sepharose four times with 2 ml PBS$^-$ containing 0.5% NP40, 0.5% DOC, and 1 mM EDTA. Then we resuspended the sample in SDS sample buffer containing -ME. We heated the sample for 10 min at 85°0 C. and separated the molecules on a 10% SDS polyacrylamide gel. We dried the gel and autoradiographed it.

CDX appeared on the autoradiograph as a single, diffuse band with molecular weight of approximately 150 kD.

EXAMPLE XII

ANTIBODIES RECOGNIZING MILAs FOR VCAM1

Polyclonal antisera were obtained from three mice that had been immunized with whole JURKAT cells. The serum from one mouse completely inhibited both RAMOS and JURKAT binding to 4 hour-induced HUVECs at room temperature. The sera from the two other mice completely inhibited RAMOS but only partially inhibited JURKAT binding under the same conditions. These data indicate that RAMOS and JURKAT share a MILA, and that JURKAT exhibits at least one other MILA not shared by RAMOS.

To prepare Moabs to lymphocyte MILAs, we immunized mice against whole live RAMOS and JURKAT cells and performed fusion of spleen cells from JURKAT-immunized mice and myeloma cells in the manner described in Example VIII, above. We are screening the resulting hybridomas by the method described in Example VII, which we used successfully to obtain monoclonal antibodies to CDX. To date we have screened the conditioned medium from about 260 hybridomas for inhibition of RAMOS adhesion to HUVECs treated with TNF for 24 hours. About 25 hybridomas have shown consistent partial inhibition of adhesion, and these are currently being subcloned fo re-screening. Such antibodies may be used to both isolate and clone lymphocyte MILAs.

EXAMPLE XIII

EVIDENCE THAT VLA4 IS A VCAM1 LIGAND

We and other colleagues have performed several studies that demonstrate that VLA4 is a VCAM1 ligand and that VLA4 has separate binding sites for VCAM1 and fibronectin.

First, we showed that monoclonal antibodies against the subunits of VLA4 inhibited the attachment of VLA4-expressing cells to activated HUVECs and to COS cells transfected with VCAM1. VLA4 is composed of the subunits $_1$ and $\alpha^4$. (Hemler, 1988.) We found that a monoclonal antibody against $_1$, designated B1E11, and goat anti-$_1$ heteroantiserum completely inhibited the adhesion of RAMOS cells to activated HUVECs and transfected COS cells. A control antibody did not inhibit adhesion. Furthermore, a monoclonal antibody against the $\alpha^4$ subunit, designated HP2/1, also blocked attachment of RAMOS to these cells. Similarly, these antibodies inhibited the attachment of the VLA4-expressing T lymphoblastoid cell line HPB-ALL.

Next, we showed that transfecting cells that do not ordinarily express VLA4 with $\alpha^4$ enabled them to bind to VCAM1-expressing cells. We transfected two sets of K-562 erythroleukemic cells. One set was transfected with a cDNA coding for $\alpha^4$. (Takada et al., 1989.) The other was transfected with $\alpha^2$, which is not part of VLA4. (Takada and Hemler, 1989.) We showed that K-562 cells transfected with $\alpha^4$ were now able to bind with a monolayer of VCAM1-transfected COS cells or TNF-activated HUVECS, but parent K-562 cells and K-562 $\alpha^2$-transfected cells were not. In addition, monoclonal antibodies against $\alpha^4$ or $_1$ abolished the adhesion of $\alpha^4$-transfected K-562 cells (that normally express the $_1$ subunit) to these VCAM1-expressing cells.

Recent studies have shown that VLA4 mediates cell attachment to human plasma fibronectin (FN) through the FN CS-1 site. (Wayner et al., 1989.) We have shown that the VLA4 binding site for VCAM1 is different than its binding site for FN. First, we found that preincubation of RAMOS cells or $\alpha^4$-transfected K-652 cells with FN-40 (a soluble FN fragment) inhibited their binding with FN-40, but not with VCAM1-transfected COS cells or TNFα activated HUVECs. Second, we found that a monoclonal against VLA4, HP1/3, inhibited the binding of these cells to transfected COS cells or activated HUVECs, but not to FN-40.

EXAMPLE XIV

INHIBITOR SCREENING

One can use ELAMs and their ligands in three basic adhesion assays to screen for potential inhibitors of adhesion, such as synthetic organic chemicals, natural fermentation products, peptides, etc.:

1. Cell-Cell Adhesion Assays

A first assay would test the ability of molecules to inhibit cell-cell adhesion. One could perform this assay in 96-well microtiter plates. First, one creates a cell line that stably expresses an ELAM, for example, as described in Example V. Then one plates out these cells and adds HL-60 cells. Inhibitors are identified by their ability to inhibit HL-60 binding to the ELAM-expressing cells. One would perform an assay exactly as described for screening for monoclonal antibodies to the ELAM ligand.

2. Cell-Adhesion Protein Assays

A second assay would test the ability of a small molecule to inhibit cell binding to ELAM itself. We have developed such an assay with rsELAM1 which works in 96 well microtiter plates. These plates, made of bacteriologic plastic (e.g. Linbro/Titertek #76-232-05®), are incubated with 0.5 µg per well of rsELAM1 in 50 µl of 15 mM sodium carbonate/35 mM sodium bicarbonate, pH 9.2, overnight at 4°. The plates are then blocked for one hour at room temperature with PBS containing 10 mg/ml of bovine serum albumin, and then adhesion assays performed as described in Example VIII using, e.g., HL-60 cells, 2×10$^6$/ml, 50 µl per well. Under these conditions HL-60 cells bind well to rsELAM1, providing a convenient microassay for screening. One would identify inhibitors by their ability to inhibit HL-60 binding to the plate. Alternatively, one could use an ELAM ligand in this assay, using as the probe a cell line that stably expresses an ELAM.

Another alternative assay in this category would examine the binding of a soluble ELAM or ELAM ligand to monolayers of cells stably expressing an ELAM ligand or ELAM, respectively. The soluble molecule would be labelled with a reporter group (e.g., radioactivity, fluorescent probe, enzyme, etc.)

3. Adhesion Protein-Adhesion Protein Assays

This assay tests the ability of a small molecule to inhibit the binding of an ELAM to its ligand. One of the two molecules in soluble form, e.g., a soluble ELAM, is immobilized in the wells of a 96-well microtiter plate, and adhesion is measured by binding of the other member of the pair, e.g., an ELAM ligand labelled with a reporter group.

In each of these three assays, one detects inhibitors by their ability to inhibit adhesion.

EXAMPLE XV

VCAM1/IMMUNOGLOBULIN CONSTRUCT

We have prepared a DNA sequence which, on expression, produces an rsVCAM1/immunoglobulin fusion protein. The DNA sequence contains, from 5' to 3', VCAM1 domains 1–3 and the constant region of an IgG$_1$ heavy chain gene.

We produced a DNA fragment containing the VCAM1 domains 1–3 through nucleotide 1035 of FIG. 3 by polymerase chain reaction (PCR). (Sambrook et al., 1989) The 3'–5' primer had the sequence 5' GA GCT CGA GGC CGC ACC ATG CCT GGG AAG ATG. It is complementary to nucleotides 100–114 in FIG. 3 and contains the VCAM1 initiation codon and recognition sites for XhoI and NotI. The 5'–3' primer had the sequence 5' CT AGC TAG CGC GTT TTA CTT CAC. It is complementary to nucleotides 1016–1035 in FIG. 3, at the end of domain 3, and contains an NheI recognition site. We used these primers to amplify a segment from a plasmid containing VCAM1 coding region of AM pcDM8 clone 41. The product of this process was a DNA sequence encoding VCAM1 domains 1–3. We digested this DNA fragment with XhoI and NheI and inserted it into pAB53, which we made as follows.

We digested pJOD-s (Example VIII) with SalI and inserted a cDNA sequence encoding human rsCD4. We called this plasmid pJOD-rsT4. We partially digested pJOD-rsT4 with PvuII and SphI to delete the fragment containing the two SV40 enhancer repeats in the SV40 promoter which control transcription of the DHFR cDNA. We religated the plasmid and designated it pJOD-rsT4 delta E. Then we digested pJOD-rsT4 delta E with NheI and NotI and inserted two DNA fragments: first, an NheI-HindIII linker containing a 5' mRNA splice site and second, a DNA fragment encoding the constant region of an IgG heavy chain gene. We obtained these fragments as follows.

We synthesized an NheI-HindIII linker having the following sequence:

5' splice

5' CTA GCT TTC CAA GGT GAG TCC TA 3'

3' GA AAG GTT CCA CTC AGG ATT CGA 5'

The DNA sequence of an IgG heavy chain gene is described in Ellison et al. (1982). We isolated a fragment of this gene from an EMBL3 human genomic library (Example VIII) using an oligonucleotide probe. We digested the fragment with HindIII and NotI and isolated the fragment which included the constant heavy domains and the associated introns.

We ligated these two fragments into pJOD-rsT4 delta E and called the resulting plasmid pAB53. We digested pAB53 with XhoI and NheI to delete the rsT4 coding region. We inserted in its place the XhoI-NheI fragment encoding VCAM1 domains 1–3. We called this plasmid VCAM1-$IgG_1$.

An rsVCAM1/IgG fusion protein is expressed using this plasmid. The plasmid is transfected into CHO cells for stable expression. After transcription of this gene, the mRNA is spliced to remove the introns and upon translation, the cell produces rsVCAM-IgG fusion protein.

EXAMPLE XVI

INHIBITING VCAM1 EXPRESSION WITH AN ANTISENSE NUCLEIC ACID

We describe here an antisense nucleic acid against VCAM1 and a method for testing its ability to inhibit VCAM1 expression in induced HUVECS. An effective nucleic acid sequence for an antisense nucleic acid is one that is complementary to the coding region of the mRNA and, more particularly, to either the initiation codon, AUG, or the splice sites. (Marcus-Sekura, 1988.) Also, oligomers of about 15 nucleotides are most preferred. Thus, an effective antisense nucleic acid against VCAM1 is an oligomer with the DNA sequence 5' CCC AGG CAT TTT AAG. This would bind to nucleotides 94–108 of FIG. 3 (CAT is the antisense initiation codon.) This DNA sequence is synthesized, for example, by an automated DNA synthesizer.

The ability of this antisense nucleic acid to inhibit VCAM1 expression is tested as follows. HUVECs are grown to confluence as in Example V except that the serum used for cell growth would be heat inactivated for 30 min. at 60° to inactivate nucleases. Cells are preincubated with the oligomers at concentrations between 10 $\mu$M and 10 $\mu$M, most preferably the highest concentration having no effect on cell viability, for four to forty-eight hours. These ranges are required for effective inhibition. (Marcus-Sekura, 1988; Becker et al., 1989.) The HUVECs are then treated with 10 ng/ml TNF to induce VCAM1. About four hours later the presence of VCAM1 on the surface of the cells is tested by the adhesion assay.

EXAMPLE XVII

A HAMMERHEAD RIBOZYME WHICH RECOGNIZES VCAM1 mRNA

A hammerhead-type ribozyme which recognizes VCAM1 mRNA is prepared according to the rules of Haselhoff and Gerlach (1988) as follows. First, a cleavage site on the target mRNA is identified. Hammerhead ribozymes cleave after the sequence 5' GUX, where X is any nucleotide. The first instance of this sequence in the coding region of VCAM1 mRNA is the sixth codon: 5' AUG CCU GGG AAG AUG GUC GUG AUC CUU. An appropriate recognition sequence includes about six nucleotides of the 5' and 3' regions flanking the cleavage site. An eighteen-base recognition sequence which contains the cleavage site is 5' AAG AUG GUC GUG AUC CUU.

Then, one designs an RNA sequence for the ribozyme containing the recognition sequence and a sequence for the catalytic "hammerhead." Such a sequence is 5' AAG GAU CAC [CUGAUGAGUCCGUGAGGACGAA] AC CAU CUU. The sequence in brackets generates the catalytic "hammerhead" and the 5' and 3' flanking sequences are complementary to and bind to the recognition sequence. In a similar way, one can also design shorter recognition sequences or those for other cleavage sites in VCAM1 mRNA or the other ELAM or ELAM ligand mRNAs.

EXAMPLE XVIII

ANTI-IDIOTYPIC ANTIBODIES RECOGNIZING ELAM1 LIGANDS

We have prepared anti-idiotypic antibodies against anti-ELAM1 antibodies that bind to the ligand of ELAM1 on HL-60 cells. We immunized rabbits with protein-A-purified CDB.BB11.BC6 monoclonal (Example V) emulsified 1:1 in complete Freund's adjuvant. Twenty-six days after immunization we bled the rabbits and analyzed the anti-sera for specific antibodies using ACS. We incubated the antibody preparation with either HL-60 cells, which express a ligand for ELAM1, or RAMOS cells, which do not. We found that this antibody preparation specifically bound to the HL-60 cells and not to the RAMOS cells, indicating that it contained antibodies that recognize the ELAM1 ligand. Control anti-serum did not react with either cell line.

While we have hereinbefore described a number of embodiments of this invention, it is apparent that one of skill in the art could alter our procedures to provide other embodiments that utilize the processes and compositions of this invention.

Therefore one will appreciate that the scope of this invention is to be defined by the claims appended thereto rather than the specific embodiments that we have presented by way of example.

CITED PUBLICATIONS

Arfors, K. -E., et al., "A Monoclonal Antibody to the Membrane Glycoprotein Complex CD18 Inhibits Polymorphonuclear Leukocyte Accumulation and Plasma Leakage In Vivo", *Blood,* 69, pp. 338–40 (1987)

Aruffo, A., and Seed, B., "Molecular Cloning of a CD28 cDNA by a High Efficiency COS Cell Expression System", *Proc. Natl. Acad. Sci. USA,* 84, pp. 8573–77 (1987)

Becker, D., et al., "Proliferation of Human Malignant Melanomas Is Inhibited by Antisense Oligodeoxynucleotides Targeted Against Basic Fibroblast Growth Factor," *EMBO J.,* 8, pp. 3685–91 (1989)

Benchimol, S., et al., "Carcinoembryonic Antigen, A Human Tumor Marker, Functions as an Intercellular Adhesion Molecule", *Cell,* 57, pp. 327–34 (1989)

Bevilacqua, M. P., and M. A. Gimbrone, "Inducible Endothelial Functions in Inflammation and Coagulation", *Seminars in Thrombosis and Hemostasis,* 13, pp. 425–33 (1987)

Bevilacqua, M. P., et al., "Interleukin 1 Acts on Cultured Human Vascular Endothelium to Increase the Adhesion of Polymorphonuclear Leukocytes, Monocytes, and Related Leukocyte Cell Lines", *J. Clin. Invest.*, 76, pp. 2003–11 (1985) ("Bevilacqua I")

Bevilacqua, M. P., et al., "Endothelial-Dependent Mechanisms of Leukocyte Adhesion: Regulation by Interleukin-1 and Tumor Necrosis Factor", *Leukocyte Emigration and Its Sequelae* (S. Karger A. G., Switzerland, 1987a), pp. 79–93 ("Bevilacqua II")

Bevilacqua, M. P., et al., "Identification of an Inducible Endothelial-Leukocyte Adhesion Molecule", *Proc. Natl. Acad. Sci. USA*, 84, pp. 9238–42 (1987b) ("Bevilacqua III")

Bevilacqua, M. P., et al., "Endothelial Leukocyte Adhesion Molecule 1: An Inducible Receptor for Neutrophilis Related to Complement Regulatory Proteins and Lectins", *Science*, 243, pp. 1160–5 (1989) ("Bevilacqua IV")

Brenan, M. and C. R. Parish, "Intracellular Fluorescent Labelling of Cells for Analysis of Lymphocyte Migration", *J. Immun. Meth.*, 74, pp. 31–38 (1984)

Capon, D. J., et al., "Designing CD4 Immunoadhesins for AIDS Therapy," *Nature*, 337, pp. 525–31 (1989)

Carlsson, R., and C. Glad, "Monoclonal Antibodies into the '90s," *Bio/Technology*, 7, pp. 567–73 (June 1989)

Cate, R., et al., "Isolation of the Bovine and Human Genes for Mullerian Inhibiting Substance and Expression of the Human Gene in Animal Cells", *Cell*, 45, pp. 685–98 (1986)

Cech, T. R., "Ribozymes and Their Medical Implications," *J. Amer. Med. Assn.*, 260, pp. 3030–4 (1988)

Chang et al., "Recombination Following Transformation of *Escherichia coli* by Heteroduplex Plasmid DNA Molecules," *Gene*, 29, pp. 255–61 (1984)

Cotran, R. S., et al., "Induction and Detection of a Human Endothelial Activation Antigen In Vivo", *J. Exp. Med.*, 164, pp. 661–66 (1986)

Cotran, R. S., and J. S. Pober, "Endothelial Activation: Its Role in Inflammatory and Immune Reactions," in *Endothelial Cell Biology*, Simionescu and Simionescu, Eds., Plenum Press, New York (1988), pp. 335–47

Dana, N., et al., "Mol Surface Glycoprotein: Structure, Function and Clinical Importance", *Pathol. Immunopathol. Res.*, 5, pp. 371–83 (1986)

Davis, M. M., "Substractive cDNA Hybridizaion and the T-Cell Receptor Gene", *Handbook of Experimental Immunology In Four Volumes*, 4th ed. Blackwell Scientific Publications, Oxford, England (1986), pp. 76.1–76.13

Davis, M. M., et al., "Cell Type-Specific cDNA Probes and the Murine I Region: The Localization and Orientation of Ad", *Proc. Natl. Acad. Sci. USA*, 81, pp. 2194–98 (1984)

Devereux, J., et al., "A Comprehensive Set of Sequence Analysis Programs for the VAX," *Nucl. Acids Res.*, 12, pp. 387–95 (1984)

Duguid, J. R., et al., "Isolation of cDNAs of Scrapie-Modulated RNAs by Subtractive Hybridization of a cDNA Library", *Proc. Natl. Acad. Sci. USA*, 85, pp. 5738–42 (1988)

Dustin, M. L., and T. A. Springer, "Lymphocyte Function-Associated Antigen-1 (LFA-1) Interaction with Intercellular Adhesion Molecule 1 (ICAM-1) Is One of at Least Three Mechanisms for Lymphocyte Adhesion to Cultured Endothelial Cells," *J. Cell. Biol.*, 107, pp. 321–33 (1988)

Dustin, M. L., et al., "Induction by IL1 and Interferon-gamma: Tissue Distribution, Biochemistry, and Function of a Natural Adherence Molecule (ICAM-1), *J. Immunol.*, 137, pp. 245–254 (1986)

Ellison, J. W., et al., "The Sequence of a Human Immunoglobulin C-gamma-i Gene," *Nucl. Acids Res.*, 10, pp. 4071–79 (1982)

Feinberg, A. P., and B. Vogelstein, "A Technique for Radiolabeling DNA Restriction Endonuclease Fragments to High Specific Activity", *Anal. Biochem.*, 132, pp. 6–13 (1983)

Feinberg, A. P., and B. Vogelstein, "A Technique for Radiolabeling DNA Restriction Endonuclease Fragments to High Specific Activity", *Anal. Biochem.*, 137, pp. 266–67 (1984) (Addendum)

Fisher, R. A., et al., "HIV Infection Is Blocked In Vitro by Recombinant Soluble CD4", *Nature*, 331, pp. 76–78 (1988)

Gimbrone, M. A., "Culture of Vascular Endothelium", *Prog. Hemostasis Thromb.*, 3, pp. 1–28 (1976)

Goding, W., ed., *Monoclonal Antibodies: Principles and Practice*, (Academic Press, New York, 1983)

Goldenberg, D. M., "Targeted Cancer Treatment," *Immunology Today*, 10, pp. 286–88 (1989)

Gubler, U. and Hoffman, B. J., "A Simple and Very Efficient Method for Generating cDNA Libraries", *Gene*, 25, pp. 263–69 (1983)

Hambor, J. E., et al., "Functional Consequences of Anti-Sense RNA-Mediated Inhibition of CD8 Surface Expression in a Human T Cell Clone," *J. Exp. Med.*, 168, pp. 1237–45 (1988)

Harlan, J. M., "Leukocyte-Endothelial Interactions," *Blood*, 65, pp. 513–25 (1985) ("Harlan I")

Harlan, J. M., "Neutrophil-Mediated Vascular Injury", *Acta Med. Scand.. Suppl.*, 715, pp. 123–29 (1987) ("Harlan II")

Harlan, J. M., et al., "The Role of Neutrophil Membrane Proteins in Neutrophil Emigration," in *Leukocyte Emigration and Its Sequelae*, H. Movat, ed.(S. Karger AG, Basel, Switzerland, 1987), pp. 94–104

Haselhoff, J., and W. L. Gerlach, "Simple RNA Enzymes with New and Highly Specific Endoribonuclease Activities," *Nature*, 334, pp. 585–591 (1988)

Hedrick, S. M., et al., "Isolation of cDNA Clones Encoding T Cell-Specific Membrane-Associated Proteins," *Nature*, 308, pp. 149–53 (1984)

Hemler, M. E., "Adhesion Protein Receptors on Hematopoietic Cells", *Immunol. Today*, 9, pp. 109–113 (1988)

Hemler, M. E., et al., "The VLA Protein Family (Characterization of Five Distinct Cell Surface Heterodimers Each with a Common 130,000 Molecular Weight Subunit)," *J. Biol. Chem.*, 262, pp. 3300–09 (1987a)

Hemler, M. E., et al., "Characterization of the Cell Surface Heterodimer VLA-4 and Related Peptides," *J. Biol. Chem.*, 262, pp. 11478–85 (1987b)

Hirt, B., "Selective Extraction of Polyoma DNA from Infected Mouse Cell Cultures", *J. Mol. Biol.*, 26, pp. 365–69 (1967)

Hough, A. and L. Sokoloff, "Pathology", Chap. 4, *Rheumatoid Arthritis*, P. D. Ustinger, N. J. Zugifler, and Ehrlich, G. E., eds., (Lippencott, Philadelphia, 1985), pp. 49–69

Hunkapiller, T. and L. Hood, "Diversity of the Immunoglobulin Gene Superfamily", *Adv. Immunol.*, 44, pp. 1–63 (1989)

Huse, W. D., et al., "Generation of a Large Combinatorial Library of the Immunoglobulin Repertoire in Phage Lambda," *Science*, 246, pp. 1275–81 (1989)

Hynes, R. O., "Integrins: A Family of Cell Surface Receptors", *Cell*, 48, pp. 549–554 (1987)

Kaldoron et al., *Nucl. Acids Res.*, 10, pp. 5161–71 (1982)

Kennedy, R. C., et al., "Anti-idiotypes and Immunity," *Sci. Am.*, 255, pp. 48–56 (July 1986)

Kurzinger, K., et al., "A Novel Lymphocyte Function-Associated Antigen (LFA-1): Cellular Distribution, Quantitative Expression, and Structure", *J. Immunol.*, 127, pp. 596–602 (1981)

Lehrach, H., et al., "RNA Molecular Weight Determinations by Gel Electrophoresis under Denaturing Conditions, a Critical Reexamination", *Biochem.*, 16, pp. 4743–51 (1977)

Lenardo, M. J. and D. Baltimore, "NF-κB: A Pleiotropic Mediator of Inducible and Tissue Specific Gene Control," *Cell*, 58, pp. 227–30 (1989)

Malech, H. L. and Gallin, J. I., "Neutrophils in Human Diseases", *N. Eng. J. Med.*, 317, pp. 687–94 (1987)

Maniatis, T., et al., Molecular Cloning: *A Laboratory Manual* (Cold Spring Harbor Laboratory, Cold Spring Harbor, N.Y., 1982)

Marcantonio, E. E., and R. O. Hynes, "Antibodies to the Conserved Cytoplasmic Domain of the Integrin β-1 Subunit React with Proteins in Vertebrates, Invertebrates and Fungi," *J. Cell. Biol*, 106, pp. 1765–72 (1988)

Marcus-Sekura, C. J., "Techniques for Using Antisense Oligonucleotides to Study Gene Expression," *Anal. Biochem.*, 172, pp. 289–95 (1988)

Marlin, S. D., and T. A. Springer, "Purified Intercellular Adhesion Molecule-1 (ICAM-1) Is a Ligand for Lymphocyte Function-Associated Antigen 1 (LFA-1)," *Cell*, 51, pp. 813–9 (1987)

Maxam, A. and W. Gilbert, "Sequencing End-Labeled DNA with Base-Specific Chemical Cleavages", *Methods in Enzymol.*, 65, pp. 499–560 (1980)

Morinaga et al., "Improvement of Oligonucleotide-Directed Site-Specific Mutagenesis Using Double-Stranded Plasmid DNA," *Bio/Technology*, 2, pp. 636–9 (1984)

Oostra et al., "Transforming Activity of Polyoma Virus Middle-T Antigen Probed by Site-Directed Mutagenesis," *Nature*, 304, pp. 456–60 (1983)

Osborn, L., et al., "Tumor Necrosis Factor α and Interleukin 1 Stimulate the Human Immunodeficiency Virus Enhancer by Activation of the Nucleus Factor κB," *Proc. Natl. Acad. Sci., U.S.A.*, 86, pp. 2336–40 (1989)

Peden, K. W. C. and D. Nathaps, "Local Mutagenesis Within Deletion Loops of DNA Heteroduplexes," *Proc. Natl. Acad. Sci., U.S.A.*, 79, 7214–17 (1982)

Pober, J. S., et al., "Overlapping Patterns of Activation of Human Endothelial Cells by Interleukin 1, Tumor Necrosis Factor, and Immune Interferon," *J. Immunol.*, 137, pp. 1895–6 (1986)

Ross, R., "The Pathogenesis of Atherosclerosis—An Update", *N. Eng. J. Med*, 314, pp. 488–500 (1986)

Rothlein, R., et al., "A Human Intercellular Adhesion Molecule (ICAM-1) Distinct from LFA-1," *J. Immunol.*, 137, pp. 1270–4 (1986)

Ruoslahti, E., "Fibronectin and its Receptors", *Ann. Rev. Biochem.*, 57, pp. 375–413 (1988)

Sambrook, J., et al., "In Vitro Amplification of DNA by Polymerase Chain Reaction," Chapter 14 in *Molecular Cloning, A Laboratory Manual*, Cold Spring Harbor Laboratory Press, Cold Spring Harbor, N.Y. (1989)

Sandri-Goldin, R. M., et al., "High Frequency Transfer of Cloned Herpes Simplex Virus Type I Sequences to Mammalian Cells by Protoplast Fusion", *Molec. and Cell Biol.*, 1, pp. 743–52 (1981)

Sargent, T. D., "Isolation of Differentially Expressed Genes", *Methods in Enzymol.*, 152, pp. 423–47 (1987)

Sato, K., et al., "A Specific DNA Sequence Controls Termination of Transcription in the Gastrin Gene," *Molec. and Cell Biol.*, 6, pp. 1032–43 (1986)

Schneider, C., et al., "A One-Step Purification of Membrane Proteins Using a High Efficiency Immunomatrix" *J. Biol. Chem.*, 257, pp. 10766–69 (1982)

Seed, B., "An LFA-3 cDNA Encodes a Phospholipid-Linked Membrane Protein Homologous to Its Receptor CD2", *Nature*, 329, pp. 840–42 (1987)

Seed, B. and A. Aruffo, "Molecular Cloning of the CD2 Antigen, the T-Cell Erythrocyte Receptor, by a Rapid Immunoselection Procedure", *Proc. Natl. Acad. Sci. USA*, 84, pp. 3365–69 (1987)

Skerra, A. and A. Pluckthun, "Assembly of a Functional Immunoglobulin $F_v$ Fragment in *Escherichia coli*," *Science*, 240, pp. 1038–1043 (1988)

Simmons et al., "ICAM, an Adhesion Ligand of LFA-1, Is Homologous to the Neural Cell Adhesion Molecule NCAM," *Nature*, 331, pp. 624–47 (1988)

Smith, C. W., et al., "Cooperative Interactions of LFA-1 and Mac-1 with Intercellular Adhesion Molecule 1 in Facilitating Adherence and Transendothelial Cell Migration of Human Neutrophils in Vitro," *J. Clin. Invest.*, 83, pp. 2008–17 (1989)

Springer, T. A., et al., "The Lymphocyte Function-Associated LFA-1, CD2, and LFA-3 Molecules: Cell Adhesion Receptors of the Immune System", *Ann. Rev. Immunol.*, 5, pp. 223–252 (1987)

Staunton, D. E., et al., "Primary Structure of ICAM-1 Demonstrates Interaction Between Members of the Immunoglobulin and Integrin Supergene Families", *Cell*, 52, pp. 925–33 (1988)

Subramani, S., et al., "Expression of the Mouse Dihydrofolate Reductase Complementary Deoxyribonucleic Acid in Simina Virus 40 Vectors," *Molec. Cell. Biol.*, 1, pp. 854–64 (1981)

Takada, Y., and M. E. Hemler, "The Primary Structure of the VLA-2/Collagen Receptor $\alpha^2$ Subunit (Platelet GP Ia): Homology to Other Integrins and the Presence of a Possible Collagen-Binding Domain," *J. Cell. Biol.*, 109, pp. 397–407 (1989)

Takada, Y., et al., "The Primary Structure of the α4 Subunit of VLA-4: Homology to Other Integrins and a Possible Cell-Cell Adhesion Function," *EMBO J.*, 8, pp. 1361–68 (1989)

Todd III, R. F., et al., "The Anti-Inflammatory Properties of Monoclonal Anti-Mol (CD11B/CD18) Antibodies in Vitro and in Vivo," in *Structure and Function of Molecules Involved in Leukocyte Adhesion*, Rosethal et al., Eds., Springer - Verlag, New York (1989) in press Vedder, N. B., et al., "A Monoclonal Antibody to the Adherence-Promoting Leukocyte Glycoprotein, CD18, Reduces Organ Injury and Improves Survival from Hemorrhagic Shock and Resuscitation in Rabbits", *J. Clin. Invest.*, 81, pp. 939–44 (1988)

von Heijne, G., "A Method for Predicting Signal Sequence Cleavage Sites", *Nucl. Acids Res.*, 14, pp. 4693–90 (1986)

Ward, E. S., et al., "Binding Activities of a Repertiore of Single Immunoglobulin Variable Domains Secreted from *Escherichia coli*," *Nature*, 341, pp. 544–46 (1989)

Wallis, W. J., and J. M. Harlan, "Effector Functions of Endothelium in Inflammatory and Immunologic Reactions," *Pathol. Immunopathol. Res.*, 5, pp. 73–103 (1986)

Wayner, E. A., et al., "Identification and Characterization of the Lymphocyte Adhesion Receptor for an Alternative Cell Attachment Domain in Plasma Fibronectin," *J. Cell. Biol.*, in press (1989)

Weintraub, H. M., "Antisense RNA and DNA," *Sci. Am.*, 262, pp. 40–46 (January 1990)

Wheeler, M. E., et al., "Cultured Human Endothelial Cells Stimulated with Cytokines or Endotoxin Produce an Inhibitor of Leukocyte Adhesion", *J. Clin. Invest.*, 82, pp. 1211–18 (1988)

White, J. and D. Littmann, "Viral Receptors of the Immunoglobulin Superfamily", *Cell*, 56, pp. 725–28 (1989)

Williams, A. and Barclay, A. N., "The Immunoglobulin Superfamily—Domains for Cell Surface Recognition", *Ann. Rev. Immunol.*, 6, pp. 381–405 (1988)

Wysocki, L. J. and V. L. Sato, "'Panning' for Lymphocytes: A Method for Cell Selection", *Proc. Natl. Acad. Sci. USA*, 75, pp. 2844–48 (1978)

Yamasaki, K., et al., "Cloning and Expression of the Human Interleukin-6 (BSF-2/IFNB2) Receptor", *Science*, 241, pp. 825–28 (1988)

Young, R. A. and R. W. Davis, "Efficient Isolation of Genes by Using Antibody Probes", *Proc. Natl. Acad. Sci. USA*, 80, pp. 1194–98 (1983) ("Young I")

Young, R. A. and R. W. Davis, "Yeast RNA Polymerase II Genes: Isolation with Antibody Probes", *Science*, 222, pp. 778–82 (1984) ("Young II")

Foreign Patent Application

Hemler, M. E. and Y. Takada, "VLA Proteins," EP 330,506, published Aug. 30, 1989.

What is claimed is:

1. An isolated VCAM1 polypeptide selected from the group consisting of the following polypeptides:
   (a) a polypeptide that consists of an amino acid sequence shown in FIG. 3 extending from amino acid number 24 (phenylalanine) to, and including, amino acid number 107 (isoleucine);
   (b) a polypeptide that consists of an amino acid sequence shown in FIG. 3 extending from amino acid number 108 (Glutamine) to, and including, amino acid number 216 (Leucine);
   (c) a polypeptide that consists of an amino acid sequence shown in FIG. 3 extending from amino acid number 217 (Glutamine) to, and including, amino acid number 309 (Alanine);
   (d) a polypeptide that consists of an amino acid sequence shown in FIG. 3 extending from amino acid number 310 (Phenylalanine) to, and including, amino acid number 412 (Leucine);
   (e) a polypeptide that consists of an amino acid sequence shown in FIG. 3 extending from amino acid number 413 (Tyrosine) to, and including, amino acid number 505 (Valine); and
   (f) a polypeptide that consists of an amino acid sequence shown in FIG. 3 extending from amino acid number 506 (Threonine) to, and including, amino acid number 597 (Asparagine); wherein said numbering begins at a proline residue (amino acid number 1) immediately adjacent to the N-terminal methionine shown in FIG. 3 and wherein said isolated VCAM1 polypeptide is essentially free of normally associated animal protein.

2. An isolated VCAM1 polypeptide selected from the group consisting of the following polypeptides:
   (a) a polypeptide that consists of an amino acid sequence shown in FIG. 3 extending from amino acid number 25 (phenylalanine) to, and including, amino acid number 108 (isoleucine);
   (b) a polypeptide that consists of an amino acid sequence shown in FIG. 3 extending from amino acid number 109 (Glutamine) to, and including, amino acid number 217 (Leucine);
   (c) a polypeptide that consists of an amino acid sequence shown in FIG. 3 extending from amino acid number 218 (Glutamine) to, and including, amino acid number 310 (Alanine);
   (d) a polypeptide that consists of an amino acid sequence shown in FIG. 3 extending from amino acid number 311 (Phenylalanine) to, and including, amino acid number 413 (Leucine);
   (e) a polypeptide that consists of an amino acid sequence shown in FIG. 3 extending from amino acid number 414 (Tyrosine) to, and including, amino acid number 506 (Valine); and
   (f) a polypeptide that consists of an amino acid sequence shown in FIG. 3 extending from amino acid number 507 (Threonine) to, and including, amino acid number 598 (Asparagine), wherein said numbering begins at an N-terminal methionine residue (amino acid number 1) shown in FIG. 3 and wherein said isolated VCAM1 polypeptide is essentially free of normally associated animal protein.

3. An isolated VCAM1b polypeptide selected from the group consisting of the following polypeptides:
   (a) a polypeptide that consists of an amino acid sequence shown in FIG. 4 extending from amino acid number 24 (phenylalanine) to, and including, amino acid number 107 (isoleucine);
   (b) a polypeptide that consists of an amino acid sequence shown in FIG. 4 extending from amino acid number 108 (Glutamine) to, and including, amino acid number 216 (Leucine);
   (c) a polypeptide that consists of an amino acid sequence shown in FIG. 4 extending from amino acid number 217 (Glutamine) to, and including, amino acid number 311 (Proline);
   (d) a polypeptide that consists of an amino acid sequence shown in FIG. 4 extending from amino acid number 312 (Phenylalanine) to, and including, amino acid number 395 (Isoleucine);
   (e) a polypeptide that consists of an amino acid sequence shown in FIG. 4 extending from amino acid number 396 (Glutamine) to, and including, amino acid number 504 (Leucine);
   (f) a polypeptide that consists of an amino acid sequence shown in FIG. 4 extending from amino acid number 505 (Tyrosine) to, and including, amino acid number 597 (Valine); and
   (g) a polypeptide that consists of an amino acid sequence shown in FIG. 4 extending from amino acid number 598 (Threonine) to, and including, amino acid number 689 (Asparagine) wherein said numbering begins at the proline (amino acid number 1) immediately adjacent to the N-terminal methionine of FIG. 4 and wherein said isolated VCAM1b polypeptide is essentially free of normally associated animal protein.

4. An isolated VCAM1b polypeptide, wherein the polypeptide is selected from the group consisting of the following polypeptides:

(a) a polypeptide that consists of an amino acid sequence shown in FIG. 4 extending from amino acid number 25 (phenylalanine) to, and including, amino acid number 108 (isoleucine);

(b) a polypeptide that consists of an amino acid sequence shown in FIG. 4 extending from amino acid number 109 (Glutamine) to, and including, amino acid number 217 (Leucine);

(c) a polypeptide that consists of an amino acid sequence shown in FIG. 4 extending from amino acid number 218 (Glutamine) to, and including, amino acid number 302 (Proline);

(d) a polypeptide that consists of an amino acid sequence shown in FIG. 4 extending from amino acid number 303 (Phenylalanine) to, and including, amino acid number 386 (Isoleucine);

(e) a polypeptide that consists of an amino acid sequence shown in FIG. 4 extending from amino acid number 387 (Glutamine) to, and including, amino acid number 505 (Leucine);

(f) a polypeptide that consists of an amino acid sequence shown in FIG. 4 extending from amino acid number 506 (Tyrosine) to, and including, amino acid number 598 (Valine); and (g) a polypeptide that consists of an amino acid sequence shown in FIG. 4 extending from amino acid number 599 (Threonine) to, and including, amino acid number 690 (Asparagine), wherein said numbering begins at the N-terminal methionine (amino acid number 1) of FIG. 4 and wherein said isolated VCAM1b polypeptide is essentially free of normally associated animal protein.

5. An isolated VCAM/ICAM fusion protein comprising (a) at least one polypeptide of claim 2 which binds to VLA4 and (b) at least one ICAM1 domain which binds to LEA1.

* * * * *